(12) United States Patent
Pastan et al.

(10) Patent No.: US 7,052,703 B1
(45) Date of Patent: May 30, 2006

(54) T-CELL RECEPTORγ ALTERNATE READING FRAME PROTEIN, (TARP) AND USES THEREOF

(75) Inventors: Ira Pastan, Potomac, MD (US); Magnus Essand, Uppsala (SE); Byungkook Lee, Potomac, MD (US); George Vasmatzis, Byron, MN (US); Curt Wolfgang, Germantown, MD (US); Ulrich Brinkmann, Weilheim (DE)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 70 days.

(21) Appl. No.: 10/031,158

(22) PCT Filed: Jul. 12, 2000

(86) PCT No.: PCT/US00/19039

§ 371 (c)(1),
(2), (4) Date: Jan. 11, 2002

(87) PCT Pub. No.: WO01/04309

PCT Pub. Date: Jan. 18, 2001

Related U.S. Application Data

(60) Provisional application No. 60/143,560, filed on Jul. 13, 1999, provisional application No. 60/157,471, filed on Oct. 1, 1999.

(51) Int. Cl.
*A61K 39/00* (2006.01)

(52) U.S. Cl. .......... 424/277.1; 350/328; 350/350; 536/23.4; 536/23.5; 514/15; 514/16; 424/185.1; 424/192.1; 424/93.1; 435/320.1; 435/372.3

(58) Field of Classification Search ............ 424/93.1, 424/192.1, 185.1, 277.1; 435/372.3, 320.1; 530/328, 350; 536/23.4, 23.5; 514/15, 16
See application file for complete search history.

(56) References Cited

U.S. PATENT DOCUMENTS

2003/0108963 A1* 6/2003 Schlegel et al. ........... 435/7.23

FOREIGN PATENT DOCUMENTS

WO    WO 01/04309 A1 * 1/2001

OTHER PUBLICATIONS

Cheng W-S, et al. Endocrinology. 2003; 144 (8): 3433-40.*
Maeda H, et al. J. Biol. Chem. Jan. 4, 2002; 279 (23): 24561-8.*
Lu J, et al. Cancer Res. Oct. 15, 2002; 62 (20): 5807-12.*
Bodey B, et al. Anticancer Res. 2000; 20: 2665-76.*
Splitler LE. Cancer Biotherapy, 1995; 10 (1): 1-3.*
Ezzell C. J NIH Res. Jan. 1995; 7: 46-9.*
Burgess WH, et al. J Cell Biol Nov. 1990; 111 (5 Pt 1): 2129-38.*
Bowie JU, et al. Science Mar. 16, 1990; 247 (4948): 1306-10.*
Lazar E, et al. Mol Cell Biol Mar. 1988; 8 (3): 1247-52.*
Skolnick J, et al. Trends Biotechnol Jan. 2000; 18 (1): 34-9.*
Ward AM. Developmental Oncol. 1985; 21: 90-106.*
Gura T. Science. 1997; 278: 1041-2.*
Tockman MS, et al. Cancer Res. 1992; 52 (Suppl.): 2711s-2718s.*
Wolfgang CD, et al. Proc Natl Acad Sci USA. Aug. 15, 2000; 97 (17): 9437-42.*
Wolfgang CD, et al. Cancer Res. Nov. 15, 2001; 61: 8122-6.*
Greenspan NS, et al. Nature Biotech. 1999; 7: 936-7.*
Boon T. Advances in Cancer Research. 1992; 58: 177-210.*
Critchfield GC. Disease Markers. 1999; 15: 108-11.*
Sidransky D. Science. Nov. 7, 1997; 278: 1054-8.*
Oh et al., "Human CTLs to wild-type and enhanced epitopes of a novel prostate and breast tumor-associated protein, TARP, lyse human breast cancer cells," *Cancer Res.* 64(7):2610-2618, 2004 (abstract only).
Wolfgang et al., "T-cell receptor gamma chain alternate reading frame protein (TARP) expression in prostate cancer cells leads to an increased growth rate and induction of caveolins and amphiregulin," *Cancer Res.* 61(22):8122-8126, 2001 (abstract only).
GenBank Accession No. AAG29337.
GenBank Accession No. AI557112.
GenBank Accession No. CAA51166.
GenBank Accession No. M27334.
GenBank Accession No. X72500.
Krangel et al., GenBank Accession No. M16768, Jan. 14, 1995.
Wolfgang et al., "TARP: A nuclear protein expressed in prostate and breast cancer cells derived from an alternate reading frame of the T cell receptor γ chain locus," *Proc. Natl. Acad. Sci USA*, 97(17):9437-9442 (2000).
Oh et al., *Cancer Research* 64:2610-2618, 2004.
Wolfgang et al., *Cancer Research* 61:8122-8126, 2001.

(Continued)

*Primary Examiner*—Stephen L. Rawlings
(74) *Attorney, Agent, or Firm*—Klarquist Sparkman LLP

(57) ABSTRACT

This invention provides nucleic acids containing sequences from a TCRγ transcript from prostate epithelial cells and many breast cancer cells and a T-cell receptor gamma Alternate Reading frame Protein ("TARP") expressed from the translation of those sequences. Vaccines made from TARP are useful in raising immune responses to cells in which the protein is expressed, including prostate cancer cells and cells of many breast cancers. The invention also provides methods for diagnosing the presence of prostate cancer and TARP-expressing breast cancers, as well as methods of administering TARP and nucleic acids encoding TARP to subjects.

31 Claims, 14 Drawing Sheets

OTHER PUBLICATIONS

GENBANK® Accession No. AAG29337.
GENBANK® Accession No. AI557112.
GENBANK® Accession No. CAA51166.
GENBANK® Accession No. M27334.
GENBANK® Accession No. X72500.
Essand et al., "High expression of a specific T-cell receptor γ transcript in epithelial cells of the prostate," *Proc. Natl. Acad. Sci. USA*, vol. 96, pp. 9287-9292 (1999).
Davodeau et al., "Secretion of Disulfide-linked Human T-cell Receptor γδ Heterodimers," *The Journal of Biological Chemistry*, vol. 268, No. 21, pp. 15455-15460 (1993).
Yoshikai, et al., "Repertoire of the human T cell gamma genes: high frequency of nonfunctional transcripts in thymus and mature T cells," *Eur. J. Immunol.* vol. 17, No. 1, pp. 119-126 (1987) (Embl. Database Entry HSTCRGAA4, Accession No. M27334).
Huang et al., "Prostate cancer expression profiling by cDNA sequencing analysis," *Genomics*, vol. 59, No. 2, pp. 178-186 (1999) (EMEST Database Entry AI557112, Accession No. AI557112).
Hawkins et al., "PEDB: the Prostate Expression Database," *Nucleic Acids Research*, vol. 27, No. 1, pp. 204-208 (1999).
Vasmatzis et al., "Discovery of three genes specifically expressed in human prostate by expressed sequence tag database analysis," *Proc. Natl. Acad. Sci. USA*, vol. 95, pp. 300-304 (1998).

\* cited by examiner

Prostate-Specific Transcript from TCRγ locus

```
          GGGCAAGAGTTGGGCAAAAAAATCAAGGTATTTGGTCCCGGAACAAAGCTTATCATTACA   60
          <----------------- J gamma 1.2 ----------------->
                                                          20
                     M  Q  M  F  P  P  S  P  L  F  F  F  L  Q  L  L  K  Q  S  S  R  R
GATAAACAACTTGATGCAGATGTTTCCCCCAAGCCCACTATTTTTCTTCCTTCAATTGCTGAAACAAAGCTCCAGAAGGC  140
<--------------------- C gamma 1 (exon CI) ---------------------------
                                                    40
 L  E  H  T  F  V  F  L  R  N  F  S  L  M  L  L  R  Y  I  G  K  K  R  R  A  T  R
TGGAACATACCTTTGTCTTCTTGAGAAATTTTTCCCTGATGTTATTAAGATACATTGGCAAGAAAAGAAGAGCAACACGA  220
----------------------------------------------------------------------
                        58
 F  W  D  P  R  R  G  T  P
                           M  K  T  N  D  T  Y  M  K  F  S  W  L  T  V  P  E  K
TTCTGGGATCCCAGGAGGGGAACACCATGAAGACTAACGACACATACATGAAATTTAGCTGGTTAACGGTGCCAGAAAAG  300
   20                                                                  40
 S  L  D  K  E  H  R  C  I  V  R  H  E  N  N  K  N  G  V  D  Q  E  I  I  F  P  P
TCACTGGACAAAGAACACAGATGTATCGTCAGACATGAGAATAATAAAAACGGAGTTGATCAAGAAATTATCTTTCCTCC  380
                           60
 I  K  T  D  V  I  T  M  D  P  K  D  N  C  S  K  D  A  N  D  T  L  L  L  Q  L
AATAAAGACGGATGTCATCACAATGGATCCCAAAGACAATTGTTCAAAAGATGCAAATGATACACTACTGCTGCAGCTCA  460
---------><------------ C gamma 1 (exon CII) ------------><-----------
                  80
 T  N  T  S  A  Y  Y  M  Y  L  L  L  L  L  K  S  V  V  Y  F  A  I  I  T  C  C  L
CAAACACCTCTGCATATTACATGTACCTCCTCCTGCTCCTCAAGAGTGTGGTCTATTTTGCCATCATCACCTGCTGTCTG  540
------------------------- C gamma 1 (exon CIII) ----------------------
    100                       111
 L  R  R  T  A  F  C  C  N  G  E  K  S
CTTAGAAGAACGGCTTTCTGCTGCAATGGAGAGAAATCATAACAGACGGTGGCACAAGGAGGCCATCTTTTCCTCATCGG  620
------------------------------->
TTATTGTCCCTAGAAGCGTCTTCTGAGGATCTAGTTGGGCTTTCTTTCTGGGTTTGGGCCATTTCAGTTCTCATGTGTGT  700
ACTATTCTATCATTATTGTATAACGGTTTTCAAACCAGTGGGCACACAGAGAACCTCACTCTGTAATAACAATGAGGAAT  780
AGCCACGGCGATCTCCAGCACCAATCTCTCCATGTTTTCCACAGCTCCTCCAGCCAACCCAAATAGCGCCTGCTATAGTG  860
TAGACATCCTGCGGCTTCTAGCCTTGTCCCTCTCTTAGTGTTCTTTAATCAGATAACTGCCTGGAAGCCTTTCATTTTAC  940
ACGCCCTGAAGCAGTCTTCTTTGCTAGTTGAATTATGTGGTGTGTTTTTCCGTAATAAGCAAAATAAATTTAAAAAAATG 1020
AAAAGTT 1027
```

Underlined sequences are:
- Transcription Initiation Site (within GCAAGAG sequence)
- Polyadenylation Signal (AATAAA)

Double Underlined sequences are:
- Possible Translation Initiation Codons (ATG)

FIG. 1

TABLE 1. Primers (→) used for analysis of the prostate TCRγ transcript

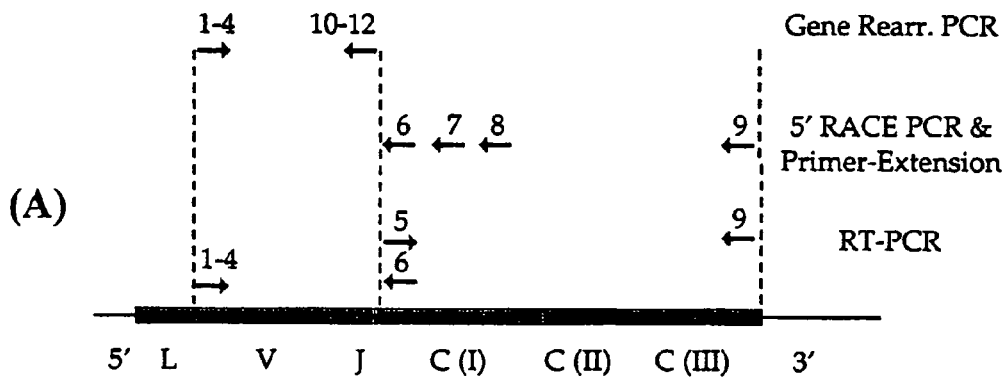

| Name | Annealing | Primer Sequence 5' -> 3' |
|---|---|---|
| 1. TCRVγI.F | Vγ, subgroup I | AACTTGGAAGGGRGAACRAAGTCAGTC |
| 2. TCRVγII.F | Vγ, subgroup II | AGTACTAAAACGCTGTCAAAAACAGCC |
| 3. TCRVγIII.F | Vγ, subgroup III | TTGGACTTGGATTATCAAAAGTGG |
| 4. TCRVγIV.F | Vγ, subgroup IV | TTGGGCAGTTGGAACAACCTGAAA |
| 5. TCRCγ.F | Cγ, exon CI | GATAAACAACTTGATGCAGATGTTTCCC |
| 6. TCRCγ.R1 | Cγ, exon CI | GGGAAACATCTGCATCAAGTTGTTTATC |
| 7. TCRCγ.R2 | Cγ, exon CI | CTGGAGCTTTGTTTCAGCAATTGAAGG |
| 8. TCRCγ.R3 | Cγ, exon CI | CTCAAGAAGACAAAGGTATGTTCCAGC |
| 9. TCRCγ.R4 | Cγ, exon CIII | TTATGATTTCTCTCCATTGCAGCAG |
| 10. TCRJγ1.1.R | Jγ1.1 | GAAGTTACTATGAGCTTAGTCCCTT |
| 11. TCRJγ1.2.R | Jγ1.2 | AAGCTTTGTTCCGGGACCAAATAC |
| 12. TCRJγ1.3.R | Jγ1.3 | TACCTGTGACAACAAGTGTTGTTC |
|  |  | R=A+G |

MQMFPPSPLFFFLQLLKQSSRR

LEHTFVFLRNFSLMLL<u>RYIGKKR</u>

<u>RATR</u>FWDPRRGTP

B.

| TARP | G | K | K | R | R | A | T | R | F | W | D | P | R | R | G | T |
|------|---|---|---|---|---|---|---|---|---|---|---|---|---|---|---|---|
| DTUP1 | G | S | K | D | R | S | V | Q | F | W | D | P | R | N | G | T |
| YTUP1 | G | S | K | D | R | G | V | L | F | W | D | K | K | S | G | N |

FIG. 14

T-CELL RECEPTORγ ALTERNATE READING FRAME PROTEIN, (TARP) AND USES THEREOF

CROSS-REFERENCES TO RELATED APPLICATIONS

This is a § 371 U.S. national stage of PCT/US00/19039 filed Jul. 12, 2000, which was published in English under PCT Article 21(2), which in turn claims the benefit of U.S. Provisional Application 60/143,560 filed Jul. 13, 1999 and U.S. Provisional Application 60/157,471 filed Oct. 1, 1999.

STATEMENT AS TO RIGHTS TO INVENTIONS MADE UNDER FEDERALLY SPONSORED RESEARCH AND DEVELOPMENT

Not applicable.

BACKGROUND OF THE INVENTION

This invention is directed to the fields of molecular biology and medical diagnostics and therapeutics.

Prostate cancer is the most prevalent form of human cancer and the third most common cause of cancer death in men. Methods for early detection and treatment of this disease would decrease the rate of prostate cancer deaths. Tumor-associated proteins, which are proteins expressed by malignant cells but few others, are useful as targets for detection and for intervention. Several proteins associated with prostate cancer have been identified, including prostate specific antigen (PSA).

Immunotherapy is a potent new weapon against cancer. Immunotherapy involves evoking an immune response against cancer cells based on their production of target antigens. While humoral immune responses against cancer cell antigens have uses, it is preferred to invoke a cell-mediated immune response against cancer cells. Immunotherapy based on cell-mediated immune responses involves generating a cell-mediated response to cells that produce particular antigenic determinants. Cancer cells produce various proteins that can become the target of immunotherapy. Certain cancers produce novel proteins, for example as a result of mutation, that are immunogenic. However, investigators also have discovered tumor infiltrating lymphocytes that specifically recognize un-mutated proteins of cancer cells. For example, Rosenberg et al. have shown that tumor infiltrating lymphocytes target and recognize antigenic determinants of the protein MART-1, produced by both normal melanocytes and malignant melanoma cells. Furthermore, active or passive immunotherapy directed against MART-1 or peptides of it that bind to MHC Class I molecules (epitopes of HLA A2, in particular) results in the destruction of melanoma cells as well normal cells that produce MART-1. Y. Kawakami et al., *J. Immunol.* 21:237 (1998).

Novel cancer antigens are expected to provoke an immune response because the immune system will recognize them as non-self proteins. However, the ability of the immune system to invoke an immune response against an un-mutated self protein was surprising because the immune system develops tolerance to self proteins. It is believed that this immune response is directed against antigenic determinants that normally are not exposed to the immune system in sufficient quantity to invoke either tolerance or an immune response. In cancer, however, these determinants no longer escape detection by the immune system. This may result from increased presentation of the determinants by MHC Class I molecules.

The cell-mediated immune response involves the activity of Major Histocompatibility Complex molecules. In humans, this complex is called the "HLA" ("Human Leukocyte Antigen") complex. In mice, it is referred to as the "H-2" complex. The major histocompatibility complex includes three classes of proteins, MHC class I, MHC class II and MHC class III. MHC class I molecules are expressed on the surface of nearly all nucleated cells. They present antigen peptides to $T_C$ cells (CD8+). There are three MHC class I gene loci in humans, HLA A, HLA B and HLA C. Each locus is highly polymorphic. Therefore, a person may have up to six different kinds of HLA molecules on the surface of their cells. MHC Class II proteins are expressed primarily on antigen presenting cells such as macrophages, dendritic cells and B cells, where they present processed antigenic peptides to $T_H$ cells. There are three MHC Class II gene loci in humans, HLA DP, HLA DQ and HLA DR. MHC class m proteins are associated with various immune processes, and include soluble serum proteins, components of the complement system and tumor necrosis factors. J. Kuby, Chapter 9, IMMUNOLOGY, Third Edition W.H. Freeman and Company, New York (1997).

In cancer cells as well as healthy cells, MHC class I molecules present epitopes from endogenous proteins for presentation to $T_C$ cells. HLA A, HLA B and HLA C molecules bind peptides of about 8 to 10 amino acids in length that have particular anchoring residues. The anchoring residues recognized by an HLA class I molecule depend upon the particular allelic form of the HLA molecule. A CD8+ T cell bears T cell receptors that recognize a specific epitope when presented by a particular HLA molecule on a cell. When a $T_C$ cell that has been stimulated by an antigen presenting cell to become a cytotoxic T lymphocyte contacts a cell that bears such an HLA-peptide complex, the CTL forms a conjugate with the cell and destroys it.

The presentation of peptides by MHC Class I molecules involves the cleavage of an endogenously produced protein into peptides by the proteasome, its processing through the ER and Golgi apparatus, its binding to the cleft in an MHC Class I molecule through the anchor residues of the peptide and ultimate presentation on the cell surface. Depending upon the particular anchor residues, among other things, certain peptides may bind more tightly to a particular HLA molecules than others. Peptides that bind well are referred to as "dominant" epitopes, while those that bind less well are termed "subdominant" or "cryptic" epitopes. Dominant epitopes of either self proteins or foreign proteins evoke strong tolerance or immune responses. Subdominant or cryptic epitopes generate weak responses or no responses at all. It is hypothesized that tighter binding by dominant epitopes to HLA molecules results in their denser presentation on the cell surface, greater opportunity to react with immune cells and greater likelihood of eliciting an immune response or tolerance.

Investigation has shown that in the case of the MART-1 protein, a self protein, the immune system generates the greatest CTL response against subdominant or cryptic epitopes. Y. Kawakami et al. 1997 *Immunol. Res.* 16:313. It may be that in cancer cells subdominant or cryptic epitopes are presented much more densely or in greater amounts than is normal; consequently, the immune system encounters these previously undetected epitopes, recognizes them as foreign and generates an immune response against them. Whatever the reason, exposing the immune system to large amounts of subdominant or cryptic epitopes of self proteins as a means of eliciting an immune response against cells that produce that protein is a key element of cancer immunotherapy. Of course, eliciting an immune response against a self protein will result in the destruction of both cancerous cells and healthy cells. Therefore, for such immunotherapy to succeed, the healthy cells must either be non-essential for life or have functions that are replaceable by other therapies. In the case of prostate cancers and breast cancer, surgical removal of the prostate or breast, respectively, is a frequent therapeutic intervention. In such cases, most or all of the tissue displaying a prostate or breast antigen will be a tumor cell.

SUMMARY OF THE INVENTION

We have discovered that prostate cells of epithelial origin both healthy and cancerous, transcribe a portion of an unrearranged TCRγ gene. While in vitro, this transcript resulted in two proteins, one of which is a truncated form of TCRγ, our studies show, surprisingly, that in vivo, the protein expressed is not a TCRγ protein, but a protein expressed from an alternate reading frame. Accordingly, the protein has been designated the TCRγ Alternate Reading Frame Protein, or "TARP."

We have discovered that TARP is expressed in prostate cells of epithelial origin and in prostate cancer cells. Surprisingly, we have discovered that the same protein is expressed in many breast cancer cells. TARP is therefore useful as a marker of prostate cancer cells and of breast cancer cells which express TARP ("TARP-expressing breast cancers") and as a basis for immunotherapy. This invention provides both the nucleic acids and the protein in isolated or recombinant form. Although we have now found that the protein is expressed in many breast cancer cells, it was first identified in prostate cells, and will sometimes be referred to below as prostate-specific ("PS")-TCRγ.

In one aspect, the invention provides an isolated polypeptide comprising the amino acid sequence of the TCRγ Alternate Reading frame Protein ("TARP"). The invention further provides immunogenic fragments of TARP (fragments which can raise an antibody which specifically recognizes and binds to full-length TARP or which activates a T-cell to recognize a cell expressing TARP), polypeptides with at least 90% sequence identity to TARP and which are specifically recognized by antibodies which specifically recognizes TARP, and polypeptides with at least 90% sequence identity with TARP and which, when processed and presented in the context of Major Histocompatibility Complex molecules, activate T lymphocytes against cells which express TARP. The invention further provides compositions in TARP, immunogenic fragments thereof, or peptides with at least 90% sequence identity and which meet the functional criteria noted above are present in a pharmaceutically acceptable carrier.

In another set of embodiments, the invention provides isolated, recombinant nucleic acid molecules which encode a polypeptide having the amino acid sequence of a TCRγ Alternate Reading frame Protein ("TARP"), which encode an immunogenic fragment thereof, which encode a polypeptide with at least 90% sequence identity to TARP and which is specifically recognized by an antibody which specifically recognizes TARP, or which encode a polypeptide which has at least 90% sequence identity with TARP and which, when processed and presented in the context of Major Histocompatibility Complex molecules, activates T lymphocytes against cells which express TARP.

In yet another series of embodiments, the invention provides methods comprising administering to a subject a composition, which composition is selected from the group consisting of: an isolated polypeptide having the amino acid sequence of a TCRγ Alternate Reading frame Protein ("TARP"), an immunogenic fragment thereof, a polypeptide with at least 90% sequence identity to TARP and which is specifically recognized by an antibody which specifically recognizes TARP, and a polypeptide which has at least 90% sequence identity with TARP and which, when processed and presented in the context of Major Histocompatibility Complex molecules, activates T lymphocytes against cells which express TARP.

The invention further provides methods of administering to a subject a composition, which composition is selected from the group consisting of: an isolated nucleic acid encoding TARP, an immunogenic fragment thereof, a polypeptide with at least 90% sequence identity to TARP and which is specifically recognized by an antibody which specifically recognizes TARP, and a polypeptide which has at least 90% sequence identity with TARP and which, when processed and presented in the context of Major Histocompatibility Complex molecules, activates T lymphocytes against cells which express TARP.

The invention further provides methods of administering to a subject a composition, which composition comprises an antigen presenting cell pulsed with a polypeptide comprising an epitope of TARP. Additionally, the invention provides methods of administering to a subject a composition, which composition comprises cells sensitized in vitro to TARP, an immunogenic fragment thereof, a polypeptide with at least 90% sequence identity to TARP which is specifically recognized by an antibody which specifically recognizes TARP, or a polypeptide which has at least 90% sequence identity with TARP which, when processed and presented in the context of Major Histocompatibility Complex molecules, activates T lymphocytes against cells which express TARP.

The compositions of the methods described above can be administered to a subject who suffers from prostate cancer, to a subject who suffers from breast cancer, or to a female subject who has not been diagnosed with breast cancer.

The methods further contemplate sensitizing CD8+ cells in vitro to an epitope of a TARP protein and administering the sensitized cells to the subject. The CD8+ cells may be $T_C$ cells. In some embodiments, the $T_C$ cells may be are tumor infiltrating lymphocytes.

Additionally, the methods may comprise co-administering to the subject an immune adjuvant selected from non-specific immune adjuvants, subcellular microbial products and fractions, haptens, immunogenic proteins, immunomodulators, interferons, thymic hormones and colony stimulating factors.

The methods may further comprise administering an antigen presenting cell pulsed with a polypeptide comprising an epitope of TARP or administering a nucleic acid sequence encoding polypeptide comprising an epitope of TARP, which nucleic acid is in a recombinant virus. The methods further comprise administering a nucleic acid sequence encoding a polypeptide comprising an epitope of a TARP protein.

Additionally, the methods comprise administering an expression vector that expresses a polypeptide comprising an epitope of a TARP protein, which expression vector is in a recombinant bacterial cell. Further, the methods comprise immunizing a subject with a expression vector that expresses a polypeptide comprising an epitope of a TARP protein, which expression vector is in an autologous recombinant cell.

In another aspect, this invention provides a method for detecting, in a male, a prostate cell of epithelial origin, or, in a female, a breast cancer cell, comprising detecting in a cell from said male or said female a nucleic acid transcript encoding TARP, or detecting TARP produced by translation of the transcript, whereby detection of the transcript or of the protein in a cell from said male identifies the cell as a prostate epithelial cell and whereby detection of the transcript or of the protein in a cell from said female identifies the cell as a breast cancer cell. The methods may comprise contacting RNA from the cell with a nucleic acid probe that specifically hybridizes to the transcript under hybridization conditions, and detecting hybridization. Moreover, the methods may include disrupting a cell and contacting a portion of the cell contents with a chimeric molecule comprising a targeting moiety and a detectable label, wherein the targeting moiety specifically binds to the protein, and detecting the label bound to the protein. The targeting moiety itself may also be labelled (for example, an antibody such as an scFv may have a radioactive residue).

The cell being examined may be from a lymph node, or it may be from a breast biopsy.

Finally, the invention provides antibodies that specifically bind to an epitope of a TCRγ Alternate Reading frame Protein.

BRIEF DESCRIPTION OF THE DRAWINGS

FIG. 1. Nucleotide sequence (SEQ ID NO:13) of PS-TCRγ transcript. In in vitro translation systems, this transcript produces two polypeptides. A first polypeptide has a deduced amino acid sequence beginning MQM . . . ("PS-TCRγ-1", now called "TARP," SEQ ID NO:14). This polypeptide has a predicted mass of 7.2 kD. It is translated from a reading frame which does not coincide with the natural TCRγ reading frame. A second polypeptide has a deduced amino acid sequence beginning MKT . . . ("PS-TCRγ-2" SEQ ID NO:15). It has a predicted mass of 13 kD. It is translated from the same reading frame as TCRγ and represents a truncated version of TCRγ. Single underlined sequences in the figure indicate the transcription initiation site and a polyadenylation site.

FIG. 2A) Multiple tissue dot blot showing differential expression of human TCRγ. Positive tissues are prostate (C7), small intestine (E3), spleen (E4), thymus (E5), peripheral leukocyte (E6), lymph node (E7), bone marrow (E8) and lung (F2). FIG. 2B). Northern blot showing TCRγ transcript sizes in normal tissues. Two TCRγ transcripts expressed in prostate are 1.1 kb and 2.8 kb while the predominant transcript in spleen, thymus and peripheral blood leukocytes is 1.5 kb. The film was exposed for 20 hours.

FIG. 3A) A TCRγ constant domain (TCR Cγ) cDNA probe shows the 1.1 and 2.8 kb prostate-specific transcripts (compare with FIG. 2B). The film was exposed for 20 hours. FIG. 3B) A TCRδ constant domain (TCR Cγ) cDNA probe reveals that TCRδ mRNA is not expressed in prostate while expression is seen in spleen, thymus and peripheral blood leukocytes. The film was exposed for 50 hours. FIG. 3C) A TCR Cγ cDNA probe shows that the LNCaP cell line expresses TCRγ while the PC-3 cell line does not. The film was exposed for 20 hours. Human β-actin mRNA expression was analyzed as a control.

FIG. 8. Primers used for analysis of PS-TCRγ transcript. (SEQ ID NOs:1–12).

(A) RT-PCR was performed with primers specific for TARP (top panels) or actin (bottom panels) using RNA derived from the following cell lines: prostate (LNCaP and PC3), neuroblastoma (A172), colon (COLO 205), gastric (KATO III) and breast (MCF7, BT-474, Hs57Bst, SK-BR-3, CRL-1897 and MDA-468). RT-PCR reactions performed without template are indicated as dH$_2$O. (B) PCR was performed using cDNAs derived from 12 human breast cancer tissue samples (lanes 1–12) using primers specific for TARP (top panel) or actin (bottom panel). PCR reactions performed without template are indicated as dH$_2$O. For both panels, 20% of the PCR products were run on a 1% agarose gel and visualized by ethidium bromide staining.

Figure 12:
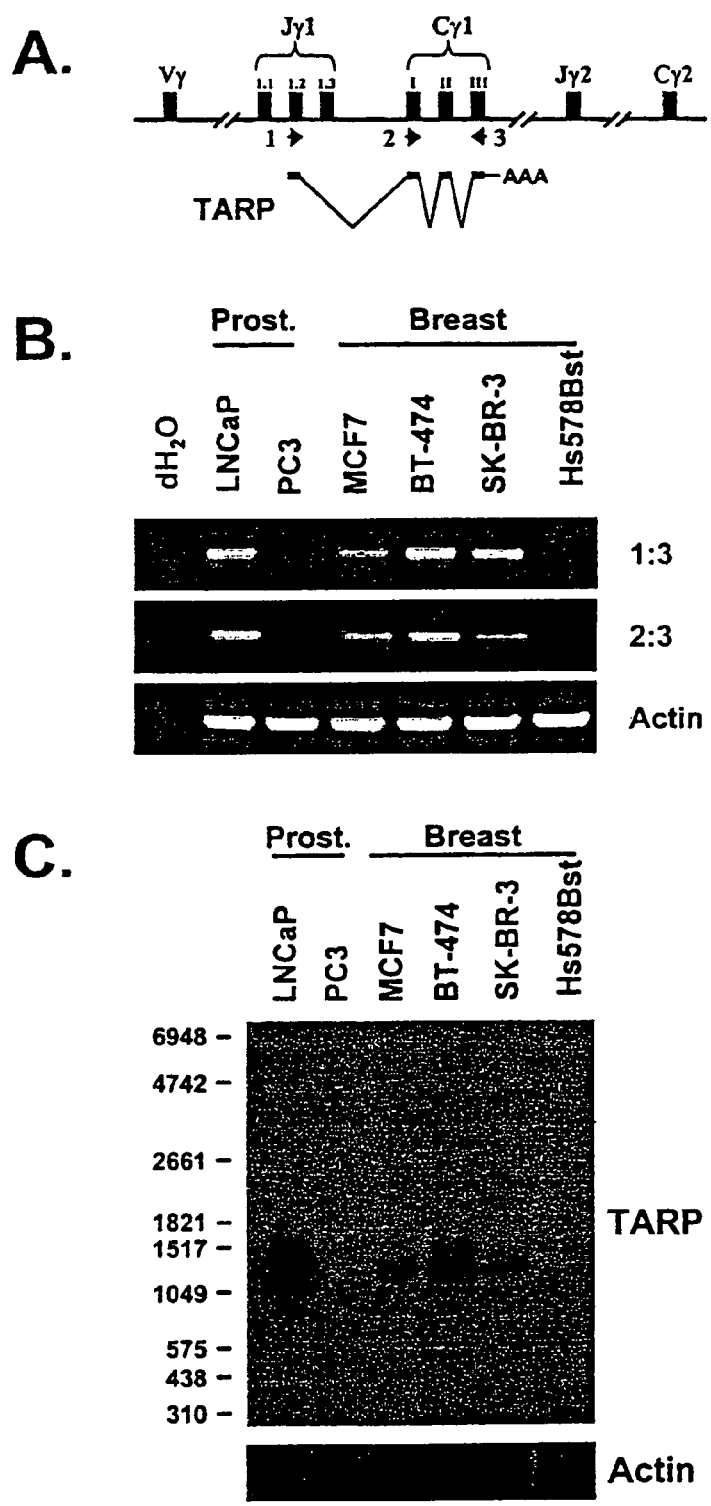

FIG. 12. The TARP transcript found in breast cell line is the same as the prostate-specific form. (A) Schematic of the TCRγ locus and how TARP is transcribed and spliced in prostate cells. Primers used for RT-PCR analysis in Panel B are indicated. (B) RT-PCR analysis of TARP mRNA expression. PCR reactions using TARP primers 1 and 3 (top panel), TARP primers 2 and 3 (middle panel) or actin primers (bottom panel) were performed with cDNAs derived from prostate cell lines (LNCaP and PC3) and breast cell lines (MCF7, BT-474, SK-BR-3 and Hs578Bst). RT-PCR reactions performed without template are indicated as dH$_2$O. 20% of the PCR products were run on a 1% agarose gel and visualized by ethidium bromide staining. (C) Northern blot analysis of TARP transcripts. 2 μg poly(A) mRNA from prostate cell lines (LNCaP and PC3) and breast cell lines (MCF7, BT-474, SK-BR-3 and Hs578Bst) were analyzed using a constant domain fragment as probe. The autoradiograph was generated after a 24-hour exposure (top panel). The same filter was stripped and analyzed with a human β-actin RNA probe to verify equal loading. The autoradiograph was generated after a 1-hour exposure (bottom panel). RNA size markers in the nucleotides are indicated on the left.

Figure 13:
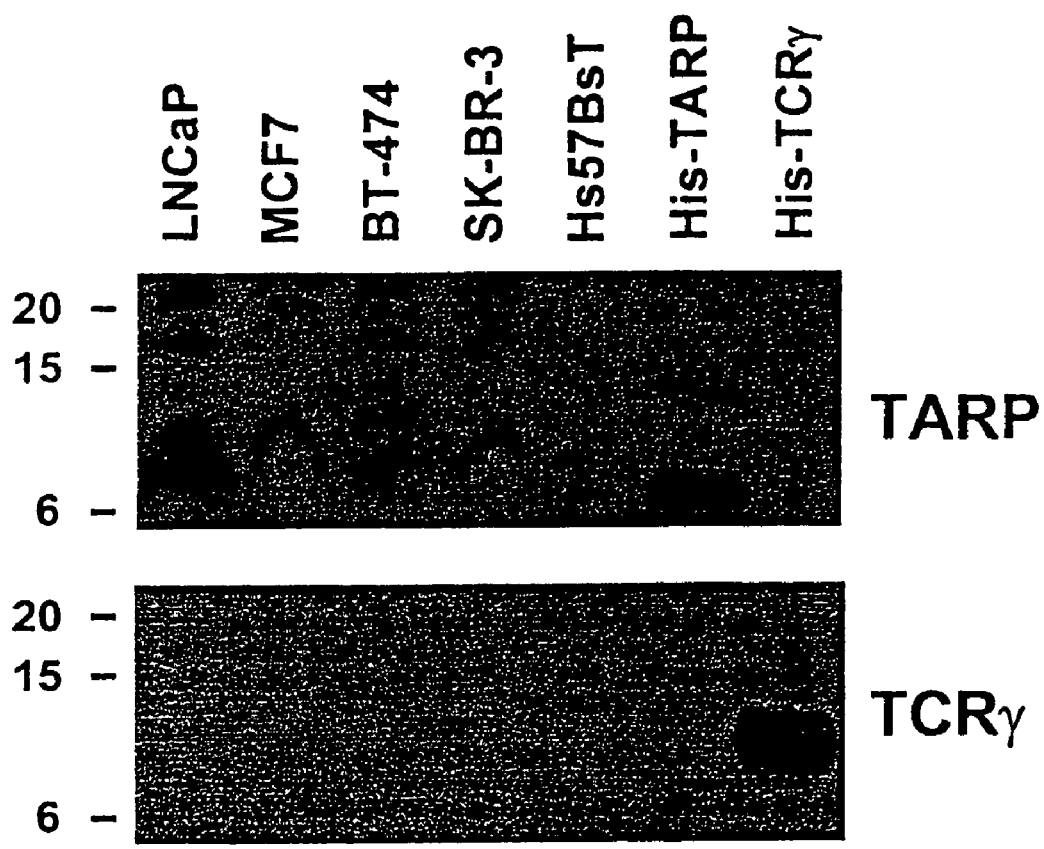

FIG. 13. TARP exists in the nuclei of breast cancer cells (A) Western blot of nuclear extracts derived from LNCaP, MCF7, BT-474, SK-BR-3 and Hs57BsT cells. 40 μg of each nuclear extract were run on a 16.5% Tris-Tricene gel and probed with an antibody against TARP (upper panel) or TCRγ (bottom panel). As a positive control, 1 μg of His-tagged TARP (His-TARP) and 100 ng of His-tagged TCRγ (His-TCRγ) were run on the gels. Size markers in kDa are indicated on the left.

FIG. 14. Potential functional domains of TARP (SEQ ID NO: 14). (A) TARP contains a potential leucine zipper motif and phosphorylation sites. A potential leucine zipper motif is indicated with boxed leucines followed by a basic region that is underlined. cAMP- and cGMP-dependent protein kinase phosphorylation sites (amino acids 46–49 and 55–58, see SEQ ID NO: 14) and protein kinase C phosphorylation sites (amino acids 19–21 and 20–22, see SEQ ID NO: 15) are outlined. (B) Protein sequence comparison of TARP with Tup 1. Amino acids sequences for TARP (42–57, SEQ ID NO: 16), *Dictyostelium dicoideum* Tup1 (dTup1, 521–536, SEQ ID NO: 17) and *Saccharomyces cerevisiae* Tup1 (yTup1, 626–660, SEQ ID NO: 18) are shown. Conserved residues are boxed.

DETAILED DESCRIPTION OF THE INVENTION

I. Introduction

Surprisingly, it has been discovered that prostate cells of epithelial origin, and cells of many breast cancers, express mRNA of the T-cell receptor gamma chain ("TCRγ"). The major TCRγ transcript in prostate has a different size than that expressed in T lymphocytes. The findings that prostate epithelial cells and many breast cancers express a high level of a transcript from a gene thought to be expressed exclusively in T lymphocytes is highly unexpected.

Because the TCRγ reading frame contains a good Kozak sequence (Kozak, M. *Cell* 44:283–92 (1986)), we initially hypothesized that a truncated TCRγ protein was encoded. Thus, it was an additional surprise to find that the TCRγ locus expressed in epithelial prostate cancer cells and breast cancer cells encodes a 7 kDa nuclear protein. Because the protein is encoded from a reading frame different from TCRγ, we have named it "TARP," for TCRγ Alternate Reading frame Protein. Besides being translated from an alternate reading frame of a transcript originating within an intron of the TCRγ locus, TARP has two other unusual features. First, it is surprising to find such a small peptide in the cell because most are usually secreted. Second, TARP lacks a good Kozak sequence In Vitro and In Vivo Uses The presence of this protein in prostate epithelial cells, prostate cancer cells, and cells of many breast cancers, creates a number of opportunities for in vitro and in vivo uses. First, antibodies raised against the protein can be used in in vitro assays to detect the presence of cells expressing TARP in a sample. For example, the Examples below demonstrate that TARP and the TARP transcript are not present, or are present at very low levels in normal breast cells, but are easily detected in cells of breast cancer which express TARP. Detection of high levels of TARP transcript or of TARP in breast cells removed from a subject therefore would be indicative of the presence of a TARP-expressing breast cancer in the subject. With respect to TARP expression in prostate cells, persons of skill in the art are aware that removal of the prostate is a frequent surgical intervention in aggressive prostate cancers. Detection of TARP in cells from an individual whose prostate has been removed is indicative that prostate cancer is present. (Persons of skill will recognize that approximately 1,000 men a year are diagnosed with breast cancer. Thus, it is not impossible that the patient also independently suffers from breast cancer. Given the fact that prostate cancer is over 200 times more common in men, and that the discussion concerns a patient already found to suffer from prostate cancer, the odds are small that the patient also independently suffers from breast cancer. The diagnosis can be confirmed by knowledge of the site from which the sample was taken, histologic and morphologic features of the cells, and other routine diagnostic criteria. In any event, since the presence of either condition demands further evaluation and monitoring, a determination that TARP-expressing cells are present in a male whose prostate has been removed is itself very useful regardless of whether the individual has prostate cancer, breast cancer, or both. Detection of TARP-expressing cells in a male who does not have prostate cancer is indicative of breast cancer.)

TARP itself, immunogenic fragments of TARP, and nucleic acids encoding TARP or immunogenic fragments thereof can also be used in vitro to activate cytotoxic T lymphocytes ("CTLs") derived from a subject to attack prostate cancer cells and TARP-expressing breast cancer cells when infused into the subject.

TARP itself, immunogenic fragments of TARP, nucleic acids encoding TARP, or immunogenic fragments thereof, can be administered to a subject, generally in a pharmaceutically acceptable carrier, to raise or to heighten an immune response to a prostate cancer or TARP-expressing breast cancer. Such compositions can be administered therapeutically, in individuals who have been diagnosed as suffering from prostate cancer or a TARP-expressing breast cancer.

As discussed below, TARP is a nuclear protein which contains structural features characteristic of proteins which regulate transcription. It is expected that modulation of TARP levels in a cell will affect the growth of the cell, the replication of the cell, or both. Thus, modulation of TARP levels can be important in controlling a cancer cell's aggressiveness. TARP levels can be reduced in a cell by various modalities which impair the ability of the RNA transcript to be translated into a protein, such as ribozymes and antisense molecules. TARP levels in a cell can also be increased. For example, expression vectors containing nucleic acids encoding TARP, driven by a strong constitutive promoter, can be introduced into a cell. The constitutive transcription of the nucleic acids results in higher levels of protein expression in the cell.

The remainder of this section describes various structural features of TARP. The text continues with definitions used in this disclosure, and continues with discussions of the selection of immunogenic fragments of TARP, the administration of TARP to subjects, the formation of antibodies against TARP, detection of TARP transcript and protein, and pharmaceutical compositions.

Structural Features of TARP

TARP contains five leucines in heptad repeats, suggesting that TARP contains a leucine zipper dimerization motif (FIG. 14A). For this to be true, TARP must contain an amphipathic helix. One indication that TARP may contain an amphipathic helix is that serine and proline residues, residues believed to serve as a helix initiator, are found immediately before the first leucine repeat. Second, many charged amino acids are found within the heptad repeats thereby giving the helix an amphipathic nature and potentially serving as salt bridges with other helicies. Even though the presence of leucines in heptad repeats is a good indication of a leucine zipper motif, there are proteins identified containing five leucines in heptad repeats that are not considered leucine zipper proteins. For example, the crystal structures for karyopherin (Chook, Y. M. et al., *Nature* 399:230–237 (1999)), *B. sterarothermophilus* pyrimidine nucleoside phosphorylase (Pugmire, M. J. et al., *Structure* 6:1467–1479 (1998)) and *T. thermophilus* phenylalanyl-tRNA synthetase (Mosyak, L. et al., *Nat. Struct. Biol.* 2:537–547 (1995)) have shown that these proteins do not contain α-helical structures in the region where the sequence contains five leucines in heptad repeats. Interaction and structure studies are needed to determine the significance of the leucine repeats found in TARP.

Another unusual feature of the TARP amino acid sequence is that a region of basic amino acids follows the potential leucine zipper motif (FIG. 14A), suggesting a possible DNA-binding motif. However, the orientation of the basic region is rather unique in that it follows the leucine repeats rather than precedes them. Most leucine zipper proteins that bind DNA have the basic region before the leucine repeats (for a review, see (Chook, Y. M. et al., *Nature* 399:230–237 (1999))). The basic region in TARP may only be functioning as a nuclear localization signal, but the fact that TARP is a nuclear protein strengthens the hypothesis that TARP may bind DNA.

To determine if TARP shares homology with any known proteins, we performed a protein BLAST search against GENBANK® (database). This search indicated that the amino acid sequence of TARP shares some homology to *Dictyostelium dicoideum* Tup1 (GENBANK® (database) accession no. AAC29438) and *Saccharomyces cerevisiae* Tup1 (Williams, F. E. et al., *Mol. Cell. Biol.* 10:6500–6511 (1990)) (FIG. 14B). Yeast Tup1 is normally found in a complex with Cyc8(Ssn6) and is required for transcriptional repression of genes that are regulated by glucose, oxygen and DNA damage (Tzamarias, D. et al., *Genes Dev.* 9:821–831 (1995)). Neither Cyc8(Ssn6) nor Tup1 binds DNA, but each acts as a part of a corepressor complex through interactions with specific DNA-binding proteins such as α2, Mig1, Rox1 and a1 (Tzamarias, D. et al., *Genes Dev.* 9:821–831 (1995)). The C'-terminal half of Tup1 contains six repeats of a 43-amino acid sequence rich in aspartate and tryptophan, known as WD-40 or β-transducin repeats (Williams, F. E. et al., *Mol. Cell. Biol.* 10:6500–6511 (1990); Fong, H. K. et al., *Proc. Natl. Acad. Sci. USA* 83:2162–2166 (1986)). WD-40 repeats have been identified in many proteins and play a role in protein—protein interactions. Importantly, Tup1 has been shown to interact with α2 through two of its WD-40 repeats (Komachi, K. et al., *Genes Dev.* 8:2857–2867 (1994)). It is interesting to note that TARP shares homology with the fifth WD-40 repeat of Tup1 (FIG. 14B). Because TARP is a nuclear protein, its homology with Tup1 suggests that TARP is a member of a functional nuclear protein complex involved in transcriptional regulation.

The TARP antibody recognizes a doublet in prostate and breast nuclear extracts (FIG. 13A). The faster 7 kDa band comigrates with the His-TARP recombinant protein, while the weaker band runs at a larger molecular weight. One possible explanation for the 9 kDa band is post-translational modifications. To determine if TARP contains any known post-translational modification sites, we analyzed the TARP amino acid sequence using the PROSITE program of the *Swiss Institute of Bioinformatics* ExPASy proteomics server (Appel, R. D. et al., *Trends Biochem. Sci.* 19:248–260 (1994); Hofmann, K. et al., *Nucleic Acids Res.* 27:215–219 (1999)). As shown in FIG. 14A, many potential phosphorylation sites were found including cAMP- and cGMP-dependent protein kinase phosphorylation sites (RRAT and RRGT) and protein kinase C phosphorylation sites (SSR and SRR). Phosphorylation has been shown in many cases to cause a protein to run at a larger apparent molecular weight on an SDS-PAGE gel. If this is the case, the results from FIG. 13 may indicate that the unmodified form is prevalent in LNCaP cells and that only the phosphorylated form is present in MCF7 and SK-BR-3 cells. TARP may therefore be post-translationally modified when expressed in prostate and breast cancer cells.

Our initial studies of the TARP transcript did not reveal TARP expression in the breast (Essand, M. et al., *Proc. Natl. Acad. Sci. USA* 96:9287–9292 (1999)). One possible explanation is that TARP is expressed at low levels in the normal breast and is difficult to detect. As described in the Results section, very weak signals were detected in a PCR analysis of normal breast samples as compared to the strong signals detected in the cancer samples. Therefore, the presence of TARP in breast cancer cells may indicate that TARP expression is induced after the oncogenic transformation of breast cells. In addition, the existence of TARP in breast cancer cells may indicate that TARP is regulated by estrogen. This hypothesis is strengthened by the identification of an element within the intronic promoter of TARP that combines an androgen response element (ARE) with an estrogen response element (ERE). This hybrid element consists of two half-sites specific to the ARE at the 5' end and to the ERE at the 3' end [(Zilliacus, J. et al., *Mol. Endocrinol.* 9:389–400 (1995)) and unpublished data)]. Additional experiments are needed to determine if estrogen regulates TARP. There are instances, however, where mutant AREs cause the expression of certain prostate-specific genes in breast tumors. For example, prostate specific antigen (PSA) has been shown to be expressed in breast tumors (Majumdar, S. et al., *Br. J. Cancer* 79:1594–1602 (1999)). Molecular analysis of the aberrant expression of PSA lead to the discovery of a single point mutation in one of the AREs found within the PSA promoter. It is believed that this mutation leads to the loss of androgen-regulated PSA expression in breast tumors (Majumdar, S. et al., *Br. J. Cancer* 79:1594–1602 (1999)). It is unclear at this time whether a similar mutation in the TARP promoter occurs in the three breast cell lines tested.

Figure 10:
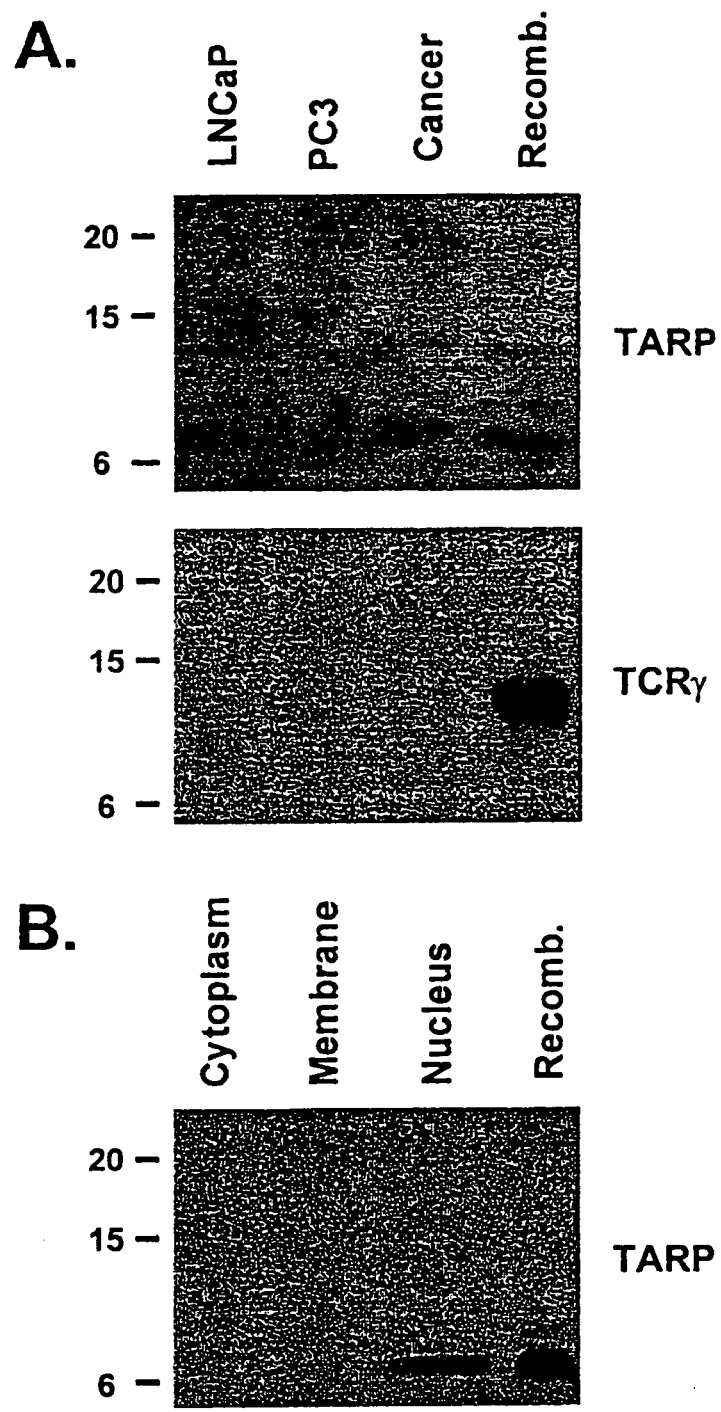
FIG. 10. TARP is nuclear protein expressed in prostate extracts. Western blot of protein extracts derived from LNCaP cells, PC3 cells or a prostate tumor sample (Cancer). 20 μg of each protein extract were run on a 16.5% Tris-Tricene gel and probed with an antibody against TARP (top panel) or TCRγ (bottom panel). As a positive control, 1 μg of His-tagged TARP (top panel) or 100 ng of His-tagged TCRγ (bottom panel) were run on the gel (Recomb.). Size markers in kDa are indicated on the left. (B) Western blot of the cytoplasmic fraction (Cytoplasm), membrane fraction (Membrane) and nuclear fraction (Nucleus,) of LNCaP cells. 40 μg of each fraction were run on a 16.5% Tris-Tricene gel and probed with an antibody against TARP. As a positive control, 1 μg of His-tagged TARP was run on the gel (Recomb.). Size markers in kDa are indicated on the left.

The prostate is dependent on androgens for maintenance of its structure and function. When prostate cells become malignant, they often lose their androgen dependence. In this study, we used two prostate cell lines that differ in their dependence on androgen for growth: LNCaP and PC3 cells. The androgen receptor is present in the androgen-dependent LNCaP cell line, but is absent in the androgen-independent PC3 cell line (Tilley, W. D. et al., *Cancer Res.* 50:5382–5386 (1990)). As shown in FIG. 10, TARP is expressed in LNCaP cells but not in PC3 cells. This result suggests that TARP expression may be regulated by androgen stimulation. The identification of an ARE-like element within the TARP promoter strengthens the idea that TARP is induced by androgens. Expression in LNCaP cell but not in PC3 cells suggests that TARP is important in regulating androgen-dependent responses.

II. Definitions

Unless defined otherwise, all technical and scientific terms used herein have the meaning commonly understood by a person skilled in the art to which this invention belongs. The following references provide a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al (eds.), Springer Verlag (1991); and Hale & Marham, THE HARPER COLLINS DICTIONARY OF BIOLOGY (1991). As used herein, the following terms have the meanings ascribed to them unless specified otherwise.

"T cell receptor" refers to a heterodimer found on the surface of T cells comprising an a chain and a β chain or a γ and a δ chain. T cell receptors recognize processed antigens associated with MHC molecules.

"T-cell receptor γ Alternate Reading frame Protein" and "TARP" refer to the polypeptide whose sequence is set forth, e.g., in FIG. 1. The polypeptide is translated from a form of the T-cell receptor γ gene present as a transcript in prostate cells of epithelial origin, in prostate cancer cells, and in many breast cancers. Since "TARP" is an acronym the last part of which stands for the word "protein," "TARP protein" is redundant.

As used herein, nucleic acid transcripts from which TARP can be translated are referred to as "TARP nucleic acids" or "nucleic acids encoding TARP." The gene from which TARP is transcribed is referred to herein as a "TARP gene."

As used herein, an "immunogenic fragment" of TARP refers to a portion of TARP which, when presented by a cell in the context of a molecule of the Major Histocompatibility Complex, can in a T-cell activation assay, activate a T-lymphocyte against a cell expressing TARP. Typically, such fragments are 8 to 12 contiguous amino acids of TARP in length, although longer fragments may of course also be used.

In the context of comparing one polypeptide to another, "sequence identity is determined by comparing the sequence of TARP, as the reference sequence, to a test sequence. Typically, the two sequences are aligned for maximal or optimal alignment.

A "ligand" is a compound that specifically binds to a target molecule.

A "receptor" is compound that specifically binds to a ligand.

"Cytotoxic T lymphocytes" ("CTLs") are important in the immune response to tumor cells. CTLs recognize peptide epitopes in the context of HLA class I molecules that are expressed on the surface of almost all nucleated cells.

Tumor-specific helper T lymphocytes ("HTLs") are also known to be important for maintaining effective antitumor immunity. Their role in antitumor immunity has been demonstrated in animal models in which these cells not only serve to provide help for induction of CTL and antibody responses, but also provide effector functions, which are mediated by direct cell contact and also by secretion of lymphokines (e.g., IFNγ and TNF-α).

"Antibody" refers to a polypeptide ligand comprising at least a light chain or heavy chain immunoglobulin variable region which specifically recognizes and binds an epitope (e.g., an antigen). This includes intact immunoglobulins and the variants and portions of them well known in the art such as, Fab' fragments, F(ab)'$_2$ fragments, single chain Fv proteins ("scFv"), and disulfide stabilized Fv proteins ("dsFv"). An scFv protein is a fusion protein in which a light chain variable region of an immunoglobulin and a heavy chain variable region of an immunoglobulin are bound by a linker. Natural immunoglobulins are encoded by immunoglobulin genes. These include the kappa and lambda light chain constant region genes, the alpha, γ, delta, epsilon and mu heavy chain constant region genes, and the myriad immunoglobulin variable region genes. The term "antibody" includes polyclonal antibodies, monoclonal antibodies, chimeric antibodies and humanized antibodies, produced by immunization, from hybridomas, or recombinantly.

"Epitope" or "antigenic determinant" refers to a site on an antigen to which B and/or T cells respond. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8–10 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, Glenn E. Morris, Ed (1996).

A ligand or a receptor "specifically binds to" a compound analyte when the ligand or receptor functions in a binding reaction which is determinative of the presence of the analyte in a sample of heterogeneous compounds. Thus, the ligand or receptor binds preferentially to a particular analyte and does not bind in a significant amount to other compounds present in the sample. For example, a polynucleotide specifically binds to an analyte polynucleotide comprising a complementary sequence and an antibody specifically binds under immunoassay conditions to an antigen analyte bearing an epitope against which the antibody was raised.

"Immunoassay" refers to a method of detecting an analyte in a sample in which specificity for the analyte is conferred by the specific binding between an antibody and a ligand. This includes detecting an antibody analyte through specific binding between the antibody and a ligand. See Harlow and Lane (1988) ANTIBODIES, A LABORATORY MANUAL, Cold Spring Harbor Publications, New York, for a description of immunoassay formats and conditions that can be used to determine specific immunoreactivity.

"Vaccine" refers to an agent or composition containing an agent effective to confer a therapeutic degree of immunity on an organism while causing only very low levels of morbidity or mortality. Methods of making vaccines are, of course, useful in the study of the immune system and in preventing and treating animal or human disease.

An "immunogenic amount" is an amount effective to elicit an immune response in a subject.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-tenninus; the right-hand end of a polypeptide sequence is the carboxyl-terminus.

"Fusion protein" refers to a polypeptide formed by the joining of two or more polypeptides through a peptide bond formed by the amino tenninus of one polypeptide and the carboxyl terminus of the other polypeptide. A fusion protein may is typically expressed as a single polypeptide from a nucleic acid sequence encoding the single contiguous fusion protein. However, a fusion protein can also be formed by the chemical coupling of the constituent polypeptides.

"Conservative substitution" refers to the substitution in a polypeptide of an amino acid with a functionally similar amino acid. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Two proteins are "homologs" of each other if they exist in different species, are derived from a common genetic ancestor and share at least 70% amino acid sequence identity.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition.

"Nucleic acid" refers to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (ie., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, e.g., a "recombinant polypeptide." A recombinant nucleic acid may serve a non-coding function (e.g., promoter, origin of replication, ribosome-binding site, etc.) as well.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g. the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression cassette" refers to a recombinant nucleic acid construct comprising an expression control sequence operatively linked to an expressible nucleotide sequence. An expression cassette generally comprises sufficient cis-acting elements for expression; other elements for expression can be supplied by the host cell or in vitro expression system.

"Expression vector" refers to a vector comprising an expression cassette. Expression vectors include all those known in the art, such as cosmids, plasmids (e.g., naked or contained in liposomes) and viruses that incorporate the expression cassette.

A first sequence is an "antisense sequence" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387–395 (1984).

Another example of algorithms that are suitable for determining percent sequence identity and sequence similarity are the BLAST and the BLAST 2.0 algorithm, which are described in Altschul et al., *J. Mol. Biol.* 215:403–410 (1990) and Altschul et al., *Nucleic Acids Res.* 25:3389–3402 (1977)). Software for performing BLAST analyses is publicly available through the National Center for Biotechnology Information (http://www.ncbi.nlm.nih.gov/). The BLASTN program (for nucleotide sequences) uses as defaults a word length (W) of 11, alignments (B) of 50, expectation (E) of 10, M=5, N=4, and a comparison of both strands. The BLASTP program (for amino acid sequences) uses as defaults a word length (W) of 3, and expectation (E) of 10, and the BLOSUM62 scoring matrix (see Henikoff & Henikoff, Proc. Natl. Acad. Sci. USA 89:10915 (1989)).

"Stringent hybridization conditions" refers to 50% formamide, 5× SSC and 1% SDS incubated at 42° C. or 5× SSC and 1% SDS incubated at 65° C., with a wash in 0.2× SSC and 0.1% SDS at 65° C.

"Naturally-occuring" as applied to an object refers to the fact that the object can be found in nature. For example, an amino acid or nucleotide sequence that is present in an organism (including viruses) that can be isolated from a source in nature and which has not been intentionally modified by man in the laboratory is naturally-occurring.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

"Pharmaceutical composition" refers to a composition suitable for pharmaceutical use in a mammal. A pharmaceutical composition comprises a pharmacologically effective amount of an active agent and a pharmaceutically acceptable carrier.

"Pharmacologically effective amount" refers to an amount of an agent effective to produce the intended pharmacological result.

"Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in REMINGTON'S PHARMACEUTICAL SCIENCES, 19th Ed. (Mack Publishing Co., Easton, 1995). Preferred pharmaceutical carriers depend upon the intended mode of administration of the active agent. Typical modes of administration include enteral (e.g., oral) or parenteral (e.g. subcutaneous, intramuscular, intravenous or intraperitoneal injection; or topical, transdermal, or transmucosal administration). A "pharmaceutically acceptable salt" is a salt that can be formulated into a compound for pharmaceutical use including, e.g., metal salts (sodium, potassium, magnesium, calcium, etc.) and salts of ammonia or organic amines.

A "subject" of diagnosis or treatment is a human or non-human mammal.

"Administration" of a composition refers to introducing the composition into the subject by a chosen route of administration. For example, if the chosen route is intravenous, the composition is administered by introducing the composition into a vein of the subject.

"Treatment" refers to prophylactic treatment or therapeutic treatment.

A "prophylactic" treatment is a treatment administered to a subject who does not exhibit signs of a disease or exhibits only early signs for the purpose of decreasing the risk of developing pathology.

A "therapeutic" treatment is a treatment administered to a subject who exhibits signs of pathology for the purpose of diminishing or eliminating those signs.

"Diagnostic" means identifying the presence or nature of a pathologic condition. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis.

"Prognostic" means predicting the probable development (e.g., severity) of a pathologic condition.

III. TARP

This invention provides isolated, recombinant TARP. Because we first found isolated a prostate-specific TCRγ transcript, we initially used the terms "PS-TCRγ protein" and "PS-TCRγ polypeptide" to refer to any polypeptide that could be translated in any reading frame from the ~1.1 kb PS-TCRγ transcript. In particular, the terms referred to two proteins, PS-TCRγ-1 (SEQ ID NO:14) and PS-TCRγ-2 (SEQ ID NO:15), translated in in vitro translation systems. We have now determined that only the first of these reading frames is translated in prostate cells. Since this reading frame is not the reading frame which results in the TCRγ chain, the protein is now referred to as the "T-cell receptor Alternate Reading frame Protein." Full-length TARP is a 58 amino acid protein whose sequence is set forth in SEQ ID NO: 14 and FIG. 1.

In certain embodiments, this invention provides polypeptides comprising an epitope comprising at least 5 to at least 15 consecutive amino acids from TARP. Such proteins bind to antibodies raised against full-length TARP (in this section, references to "TARP" refer to the full-length protein unless otherwise required by context). In other embodiments, this invention provides fusion proteins comprising a first and second polypeptide moiety in which one of the protein moieties comprises an amino acid sequence of at least 5 amino acids identifying an epitope of TARP. In one embodiment the TARP moiety is all or substantially all of TARP. The other moiety can be, e.g., an immunogenic protein. Such fusions also are useful to evoke an immune response against TARP. In other embodiments this invention provides TARP-like peptides ("TARP analogs") whose amino acid sequences are at least 90% identical to TARP (although they may have 91%, 92%, 93%, 94%, 95%, or even higher sequence identity to TARP) and which are specifically bound by antibodies which specifically bind to TARP. In yet other embodiments this invention provides TARP-like peptides (also sometimes referred to herein as "TARP-analogs") whose amino acid sequences are at least 90% identical to TARP (although they may have 91%, 92%, 93%, 94%, 95%, or even higher sequence identity to TARP) and which activate T-lymphocytes to cells which express TARP. Such proteins are useful as immunogens to break tolerance to PS-TCRγ proteins.

In another embodiment, the polypeptide comprises an epitope that binds an MHC molecule, e.g., an HLA molecule or a DR molecule. These molecules bind polypeptides having the correct anchor amino acids separated by about eight or nine amino acids. These peptides can be identified by inspection of the amino acid sequence of TARP and by knowledge of the MHC binding motifs, well known in the art.

TARP, immuonogenic fragments thereof, and TARP analogs, can be synthesized recombinantly. Immunogenic fragments of TARP and the 58-residue TARP itself, can also be chemically synthesized by standard methods. If desired, polypeptides can also be chemically synthesized by emerging technologies. One such process is described in W. Lu et al., *Federation of European Biochemical Societies Letters.* 429:31–35 (1998).

IV. TARP Nucleic Acids

In one aspect this invention provides an isolated, recombinant nucleic acid molecule comprising a nucleotide sequence encoding the TARP polypeptide (see, e.g., FIG. 1). This nucleic acid is useful for expressing TARP, which can then be used, for example, to raise antibodies for diagnostic purposes. As noted, the nucleic acid molecule has three reading frames, each of which encodes different polypeptides defined by different open reading frames. In the embodiments contemplated herein, the reading frame of interest is the one which encodes TARP.

As noted, two reading frames were translated in in vitro translation systems. A nucleotide sequence of the ~1.1 kb PS-TCRγ transcript (SEQ ID NO:13) as obtained from LNCaP cDNA and the deduced amino acid sequence when the transcript is translated from the initiation codon at nucleotide position 74 (PS-TCRγ-1, SEQ ID NO:14) and nucleotide position 247 (PS-TCRγ-2, SEQ ID NO:15) are presented in FIG. 1. The startpoint of transcription (underlined) is within the 10 first nucleotides of the Jγ1.2 segment. The sequence data is available from EMBL/GenBank/DDBJ under accession number AF151103. It should be noted that it has now been determined that the actual "+1" site is the sixth nucleotide in the sequence set forth in FIG. 1.

The practitioner can use this sequence to prepare PCR primers for isolating nucleotide sequences of this invention. LNCaP cells are useful sources of cDNA for sequences of the ~1.1 kb transcript. Genomic DNA from a human cell that has not undergone TCRγ gene rearrangement, for example, cells other than T-lymphocyte precursors, are useful for longer sequences that can be processed, upon transcription, into the ~1.1 kb transcript. The sequence can be modified to engineer a nucleic acid encoding related molecules of this invention using well known techniques.

A nucleic acid comprising sequences of this invention can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule.

A wide variety of cloning and in vitro amplification methodologies are well-known to persons skilled in the art. PCR methods are described in, for example, U.S. Pat. No. 4,683,195; Mullis et al. (1987) *Cold Spring Harbor Symp. Quant. Biol.* 51:263; and Erlich, ed., PCR TECHNOLOGY, (Stockton Press, NY, 1989). Polynucleotides also can be isolated by screening genomic or cDNA libraries with probes selected from the sequences of the desired polynucleotide under stringent hybridization conditions.

Engineered versions of the nucleic acids can be made by site-specific mutagenesis of other polynucleotides encoding the proteins, or by random mutagenesis caused by increasing the error rate of PCR of the original polynucleotide with 0.1 mM $MnCl_2$ and unbalanced nucleotide concentrations.

1. Expression Vectors

This invention also provides expression vectors for expressing polypeptides encoded by TARP transcript.

Expression vectors can be adapted for function in prokaryotes or eukaryotes by inclusion of appropriate promoters, replication sequences, markers, etc. for transcription and translation of mRNA. The construction of expression vectors and the expression of genes in transfected cells involves the use of molecular cloning techniques also well known in the art. Sambrook et al., MOLECULAR CLONING—A LABORATORY MANUAL, Cold Spring Harbor Laboratory, Cold Spring Harbor, N.Y., (1989) and CURRENT PROTOCOLS IN MOLECULAR BIOLOGY, F. M. Ausubel et al., eds., (Current Protocols, a joint venture between Greene Publishing Associates, Inc. and John Wiley & Sons, Inc.) Useful promoters for such purposes include a metallothionein promoter, a constitutive adenovirus major late promoter, a dexamethasone-inducible MMTV promoter, a SV40 promoter, a MRP polIII promoter, a constitutive MPSV promoter, a tetracycline-inducible CMV promoter (such as the human immediate-early CMV promoter), and a constitutive CMV promoter. A plasmid useful for gene therapy can comprise other functional elements, such as selectable markers, identification regions, and other genes.

Expression vectors useful in this invention depend on their intended use. Such expression vectors must, of course, contain expression and replication signals compatible with the host cell. Expression vectors useful for expressing bioactive conjugates include viral vectors such as retroviruses, adenoviruses and adeno-associated viruses, plasmid vectors, cosmids, and the like. Viral and plasmid vectors are preferred for transfecting mammalian cells. The expression vector pcDNA1 (Invitrogen, San Diego, Calif.), in which the expression control sequence comprises the CMV promoter, provides good rates of transfection and expression. Adeno-associated viral vectors are useful in the gene therapy methods of this invention.

A variety of means are available for delivering polynucleotides to cells including, for example, direct uptake of the molecule by a cell from solution, facilitated uptake through lipofection (e.g., liposomes or immunoliposomes), particle-mediated transfection, and intracellular expression from an expression cassette having an expression control sequence operably linked to a nucleotide sequence that encodes the inhibitory polynucleotide. See also U.S. Pat. No. 5,272,065 (Inouye et al.); METHODS IN ENZYMOLOGY, vol. 185, Academic Press, Inc., San Diego, Calif. (D. V. Goeddel, ed.) (1990) or M. Krieger, GENE TRANSFER AND EXPRESSION—A LABORATORY MANUAL, Stockton Press, New York, N.Y., (1990). Recombinant DNA expression plasmids can also be used to prepare the polynucleotides of the invention for delivery by means other than by gene therapy, although it may be more economical to make short oligonucleotides by in vitro chemical synthesis.

The construct can also contain a tag to simplify isolation of the protein. For example, a polyhistidine tag of, e.g., six histidine residues, can be incorporated at the amino terminal end of the protein. The polyhistidine tag allows convenient isolation of the protein in a single step by nickel-chelate chromatography.

2. Recombinant Cells

The invention also provides recombinant cells comprising an expression vector for expression of the nucleotide sequences of this invention. Host cells can be selected for high levels of expression in order to purify the protein. The cells can be prokaryotic cells, such as E. coli, or eukaryotic cells. Useful eukaryotic cells include yeast and mammalian cells. The cell can be, e.g., a recombinant cell in culture or a cell in vivo.

Cells expressing TARP are useful for active or passive immunization of subjects against cells expressing these peptides. In certain embodiments, the cells are bacterial cells. In one version of active immunization, recombinant cells are autologous cells of the subject that can present the polypeptides in association with HLA molecules. For example, antigen presenting cells are useful for this purpose. In this case, it is preferable to use "autologous cells," that is, cells derived from the subject. Such cells are MHC compatible. The TARP-encoding nucleotide sequence should be placed under the control of a constitutive promoter in such cells because one goal is to express the polypeptides in high density on the cell surface, preferably more densely than they are expressed in healthy prostate epithelial cells.

V. Method of Eliciting a Cell-Mediated Immune Response Against Cells Expressing TARP TARP is expressed by prostate cancer cells of epithelial origin and by cells of many breast cancers. Therefore, TARP can be used as a target of intervention in the treatment of prostate cancer and TARP-expressing breast cancers, as well as a marker for cancer cells that have metastasized from the prostate or breast, respectively. This invention provides methods of treating prostate cancer and TARP-expressing breast cancers with immunotherapy. The methods involve immunizing a subject against TARP, thereby eliciting a cell-mediated immune response against cells expressing TARP. Immunization can be active or passive. In active immunization, the immune response is elicited in the subject in vivo. In passive immunization, $T_C$ cells activated against the polypeptide are cultured in vitro and administered to the subject. Such methods may be expected to result in the destruction of healthy epithelial prostate tissue that express TARP. However, the prostate is not an essential organ. Its loss must be counterbalanced against the chance for loss of the subject's life from the prostate cancer, and the prostate may, indeed, be surgically removed prior to institution of TARP immunotherapy. Since normal breast tissue has not been found to express TARP in significant amounts, it does not appear that immunization against TARP-expressing cells will result in the loss of normal cells in women. Thus, TARP compositions may be administered to women prophylactically to provide an immune defense in the event that a TARP-expressing breast cancer develops later.

The immunizing agent can be of full-length TARP, a peptide comprising an antigenic determinant of TARP, e.g., an immunogenic fragment of TARP, or a protein or peptide that is substantially identical to TARP. When one is attempting to elicit a cell-mediated immune response against TARP, preferred peptides comprising antigenic determinants are those peptides bearing a binding motif for an HLA molecule of the subject. These motifs are well known in the art. For example, HLA-A2 is a common allele in the human population. The binding motif for this molecule includes polypeptides with 9 or 10 amino acids having leucine or methionine in the second position and valine or leucine in the last positions. Based on the polypeptide sequence of TARP, one can identify amino acid sequences bearing motifs for any particular HLA molecule. Peptides comprising these motifs can be prepared by any of the typical methods (e.g., recombinantly, chemically, etc.). Because TARP is a self protein, the preferred amino acid sequences bearing HLA binding motifs are those that encode subdominant or cryptic epitopes. Those epitopes can be identified by a lower comparative binding affinity for the HLA molecule with respect to other epitopes in the molecule or compared with other molecules that bind to the HLA molecule.

Polypeptides that comprise an amino acid sequence from TARP that, in turn, comprise an HLA binding motif also are useful for eliciting an immune response. This is because, in part, such proteins will be processed by the cell into a peptide that can bind to the HLA molecule and that have a TARP epitope.

A complex of an HLA molecule and a peptidic antigen acts as the ligand recognized by HLA-restricted T cells (Buus, S. et al., Cell 47:1071, 1986; Babbitt, B. P. et al., Nature 317:359, 1985; Townsend, A. and Bodmer, H., Annu. Rev. Immunol. 7:601, 1989; Germain, R. N., Annu. Rev. Immunol. 11:403, 1993). Through the study of single amino acid substituted antigen analogs and the sequencing of endogenously bound, naturally processed peptides, critical residues that correspond to motifs required for specific binding to HLA antigen molecules have been identified (see, e.g., Southwood, et al., J. Immunol. 160:3363, 1998; Rammensee, et al., Immunogenetics 41:178, 1995; Rammensee et al., Sette, A. and Sidney, J. Curr. Opin. Immunol. 10:478, 1998; Engelhard, V. H., Curr. Opin. Immunol. 6:13, 1994; Sette, A. and Grey, H. M., Curr. Opin. Immunol. 4:79, 1992).

Furthermore, x-ray crystallographic analysis of HLA-peptide complexes has revealed pockets within the peptide binding cleft of HLA molecules which accommodate, in an allele-specific mode, residues borne by peptide ligands; these residues in turn determine the HLA binding capacity of the peptides in which they are present. (See, e.g., Madden, D. R. Annu. Rev. Immunol. 13:587, 1995; Smith, et al., Immunity 4:203, 1996; Fremont et al., Immunity 8:305, 1998; Stern et al., Structure 2:245, 1994; Jones, E. Y. Curr. Opin. Immunol. 9:75, 1997; Brown, J. H. et al., Nature 364:33, 1993.)

Accordingly, the definition of class I and class II allele-specific HLA binding motifs, or class I or class II supermotifs allows identification of regions within TARP that have the potential of binding particular HLA molecules.

Molecules with high levels of sequence identity to TARP are also useful to elicit an immune response. Such molecules can be recognized as "foreign" to the immune system, yet generate antibodies or CTLs that cross react with TARP. Molecules that have high sequence identity to TARP include non-human TCRγ homologs, especially those from primates. TARP analogs whose amino acid sequences are at least 90% identical to TARP (although they may have 91%, 92%, 93%, 94%, 95%, or even higher sequence identity to TARP) and which are specifically bound by antibodies which specifically bind to TARP may be used. Further useful in this regard are TARP analogs, that is, peptides whose amino acid sequences are at least 90% identical to TARP (although they may have 91%, 92%, 93%, 94%, 95%, or even higher sequence identity to TARP) and which activate T-lymphocytes to cells which express TARP.

Another molecule that is substantially homologous to a TARP antigenic determinant can be made by modifying the sequence of a natural TARP epitope so that it binds with greater affinity for the HLA molecule.

One method of identifying genes encoding antigenic determinants is as follows: TILs from a subject with metastatic cancer are grown and tested for the ability to recognize the autologous cancer in vitro. These TILs are administered to the subject to identify the ones that result in tumor regression. The TILs are used to screen expression libraries for genes that express epitopes recognized by the TILs. Subjects then are immunized with these genes. Alternatively, lymphocytes are sensitized in vitro against antigens encoded by these genes. Then the sensitized lymphocytes are adoptively transferred into subjects and tested for their ability to cause tumor regression. Rosenberg, et al., (1997) Immunol. Today 1997 18:175.

The application of these molecules is now described. These methods are also described in Rosenberg et al. (1997) Immunol. Today 18:175 and Restifo et al. (1999) Oncology 11:50.

One method of invoking an immune response involves immunizing the subject with a polypeptide comprising an antigenic determinant from TARP, either alone or, more preferably, combined with an adjuvant, such as Freund's incomplete adjuvant, lipids or liposomes, gp96, Hsp70 or Hsp90. The polypeptide can be TARP, an antigenic fragment of TARP, a fusion protein comprising the antigenic determinant, or a peptide comprising a sequence substantially identical to such an antigenic determinant.

Another method involves pulsing a polypeptide comprising an epitope from TARP onto antigen presenting cells and administering the cells to the subject.

In another method, a recombinant virus containing a nucleic acid sequence encoding a polypeptide comprising an antigenic determinant from TARP in an expression cassette is administered to the subject. The virus optionally also can encode cytokines (e.g., IL-2), a costimulatory molecule or other genes that enhance the immune response. The virus can be, for example, adenovirus, fowlpox virus or vaccinia virus. Upon infection, the infected cells will express the TARP peptide and express the antigenic determinant on the cell surface in combination with the HLA molecule which binds peptides having the same motif as the antigenic determinant. These cells will then stimulate the activation of CTLs that recognize the presented antigen, resulting in destruction of cancer cells that also bear the determinant.

In another method, the subject is immunized with naked DNA encoding a polypeptide comprising an antigenic determinant from TARP by, e.g., intramuscular, biolistic injection or linked to lipids. Such methods have been shown to result in the stimulation of a cell-mediated response against cells that express the encoded polypeptide.

In another method, a recombinant bacteria that expresses the epitope, such as Bacillus Calmette-Guerin (BCG), Salmonella or Listeria, optionally also encoding cytokines, costimulatory molecules or other genes to enhance the immune response, is administered to the subject.

In another method, cells expressing the antigen are administered to the subject. This includes, for example, dendritic cells pulsed with TARP epitopes, cells transfected with polypeptides comprising TARP antigenic determinants, HLA and B7 genes. The multiple transfection results in the production of several components necessary for presenting the antigenic determinant on the cell surface. In one embodiment, the molecule is a fusion protein in which the polypeptide bearing the antigenic determinant is fused to an HLA molecule (usually through a linker) so as to improve binding of the peptide to the HLA molecule. In one embodiment, the cell is an antigen presenting cell. Preferably, the cells are eukaryotic cells, more preferably, mammalian cells, more preferably, human cells, more preferably autologous human cells derived from the subject.

In another method, antigen presenting cells (APCs) are pulsed or co-incubated with peptides comprising an epitope from TARP in vitro. These cells are used to sensitize CD8 cells, such as tumor infiltrating lymphocytes from prostate cancer tumors or peripheral blood lymphocytes. The TILs or PBLs preferably are from the subject. However, they should at least be MHC Class-I restricted to the HLA types the subject possesses. The sensitized cells are then administered to the subject.

In a supplemental method, any of these immunotherapies is augmented by administering a cytokine, such as IL-2, IL-3, IL-6, IL-10, IL-12, IL-15, GM-CSF, interferons.

In addition to the methods for evaluating immunogenicity of peptides set forth above, immunogenicity can also be evaluated by: evaluation of primary T cell cultures from normal individuals (see, e.g., Wentworth, P. A. et al., Mol. Immunol. 32:603, 1995; Celis, E. et al., Proc. Natl. Acad. Sci. USA 91:2105, 1994; Tsai, V. et al., J. Immunol. 158: 1796, 1997; Kawashima, I. et al., Human Immunol. 59:1, 1998); by immunization of HLA transgenic mice (see, e.g., Wentworth, P. A. et al., J. Immunol. 26:97, 1996; Wentworth, P. A. et al., Int. Immunol. 8:651, 1996; Alexander, J. et al., J. Immunol. 159:4753, 1997), and by demonstration of recall T cell responses from patients who have been effectively vaccinated or who have a tumor; (see, e.g., Rehermann, B. et al., J. Exp. Med. 181:1047, 1995; Doolan, D. L. et al., Immunity 7:97, 1997; Bertoni, R. et al., J. Clin. Invest. 100:503, 1997; Threlkeld, S. C. et al., J. Immunol. 159:1648, 1997; Diepolder, H. M. et al., J. Virol. 71:6011, 1997).

In choosing CTL-inducing peptides of interest for vaccine compositions, peptides with higher binding affinity for class I HLA molecules are generally preferable. Peptide binding is assessed by testing the ability of a candidate peptide to bind to a purified HLA molecule in vitro.

To ensure that a TARP analog when used as a vaccine, actually elicits a CTL response to TARP in vivo (or, in the case of class II epitopes, elicits helper T cells that cross-react with the wild type peptides), the TARP analog may be used to immunize T cells in vitro from individuals of the appropriate HLA allele. Thereafter, the immunized cells' capacity to induce lysis of TARP sensitized target cells is evaluated.

More generally, peptides from TARP or an analog thereof (a "peptide of the invention") can be synthesized and tested for their ability to bind to HLA proteins and to activate HTL or CTL responses, or both.

Conventional assays utilized to detect T cell responses include proliferation assays, lymphokine secretion assays, direct cytotoxicity assays, and limiting dilution assays. For example, antigen-presenting cells that have been incubated with a peptide can be assayed for the ability to induce CTL responses in responder cell populations.

PBMCs may be used as the responder cell source of CTL precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived.

A method which allows direct quantification of antigen-specific T cells is staining with Fluorescein-labelled HLA tetrameric complexes (Altman et al., Proc. Natl. Acad. Sci. USA 90:10330 (1993); Altman et al., Science 274:94 (1996)). Alternatively, staining for intracellular lymphokines, interferon-γ release assays or ELISPOT assays, can be used to evaluate T-cell responses.

HTL activation may be assessed using such techniques known to those in the art such as T cell proliferation and secretion of lymphokines, e.g. IL-2 (see, e.g. Alexander et al., Immunity 1:751–761 (1994)).

VI. Antibodies Against TARP

In one aspect this invention provides a composition comprising an antibody that specifically binds TARP. Antibodies preferably have affinity of at least $10^6$ M$^{-1}$, $10^7$ M$^{-1}$, $10^8$ M$^{-1}$, or $10^9$ M$^{-1}$. This invention contemplates both polyclonal and monoclonal antibody compositions.

A number of immunogens can be used to produce antibodies that specifically bind TARP. Full-length TARP is a suitable immunogen. Typically, the immunogen of interest is a peptide of at least about 3 amino acids, more typically the peptide is at least 5 amino acids in length, preferably, the fragment is at least 10 amino acids in length and more preferably the fragment is at least 15 amino acids in length. The peptides can be coupled to a carrier protein (e.g., as a fusion protein), or are recombinantly expressed in an immunization vector. Antigenic determinants on peptides to which antibodies bind are typically 3 to 10 amino acids in length. Naturally occurring polypeptides are also used either in pure or impure form.

Recombinant polypeptides are expressed in eukaryotic or prokaryotic cells and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

Methods for producing polyclonal antibodies are known to those of skill in the art. In brief, an immunogen, preferably a purified polypeptide, a polypeptide coupled to an appropriate carrier (e.g., GST, keyhole limpet hemocyanin, etc.), or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired. See, e.g., Coligan (1991) CURRENT PROTOCOLS IN IMMUNOLOGY Wiley/Greene, N.Y.; and Harlow and Lane (1989) ANTIBODIES: A LABORATORY MANUAL Cold Spring Harbor Press, NY.

Antibodies, including binding fragments and single chain recombinant versions thereof, against predetermined fragments of TARP are raised by immunizing animals, e.g., with conjugates of the fragments with carrier proteins as described above.

Monoclonal antibodies are prepared from cells secreting the desired antibody. These antibodies are screened for binding to normal or modified polypeptides, or screened for agonistic or antagonistic activity. In some instances, it is desirable to prepare monoclonal antibodies from various mammalian hosts, such as mice, rodents, primates, humans, etc. Description of techniques for preparing such monoclonal antibodies are found in, e.g., Stites et al. (eds.) BASIC AND CLINICAL IMMUNOLOGY (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495–497.

Other suitable techniques involve selection of libraries of recombinant antibodies in phage or similar vectors. See, Huse et al. (1989) *Science* 246: 1275–1281; and Ward, et al. (1989) *Nature* 341: 544–546.

Also, recombinant immunoglobulins may be produced. See, U.S. Pat. No. 4,816,567 (Cabilly); and Queen et al. (1989) *Proc. Nat'l Acad. Sci. USA* 86: 10029–10033.

Frequently, the polypeptides and antibodies will be labeled by joining, either covalently or non-covalently, a substance which provides for a detectable signal. A wide variety of labels and conjugation techniques are known and are reported extensively in both the scientific and patent literature. Thus, an antibody used for detecting an analyte can be directly labeled with a detectable moiety, or may be indirectly labeled by, for example, binding to the antibody a secondary antibody that is, itself directly or indirectly labeled.

The antibodies of this invention are also used for affinity chromatography in isolating TARP. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified TARP is released.

An alternative approach is the generation of humanized immunoglobulins by linking the CDR regions of non-human antibodies to human constant regions by recombinant DNA techniques. See U.S. Pat. No. 5,585,089 (Queen et al.).

A further approach for isolating DNA sequences which encode a human monoclonal antibody or a binding fragment thereof is by screening a DNA library from human B cells according to the general protocol outlined by Huse et al., *Science* 246:1275–1281 (1989) and then cloning and amplifying the sequences which encode the antibody (or binding fragment) of the desired specificity. The protocol described by Huse is rendered more efficient in combination with phage display technology. See, e.g., WO 91/17271 (Dower et al.) and WO 92/01047 (McCafferty et al.). Phage display technology can also be used to mutagenize CDR regions of antibodies previously shown to have affinity for TARP. Antibodies having improved binding affinity are selected.

In another embodiment of the invention, fragments of antibodies against TARP or protein analogs are provided. Typically, these fragments exhibit specific binding to TARP similar to that of a complete immunoglobulin. Antibody fragments include separate heavy chains, light chains Fab, Fab'F.(ab')2 and Fv. Fragments are produced by recombinant DNA techniques, or by enzymic or chemical separation of intact immunoglobulins.

VII. Chimeric Molecules that Target TARP

This invention provides chimeric molecules that target TARP. The chimeric molecules comprise a targeting moiety and an effector moiety. The chimeric proteins are useful in the detection of the polypeptide and cells that bear it.

A. Targeting Moiety

The chimeric molecules of this invention comprise a targeting moiety. The targeting moiety comprises a ligand that specifically binds to TARP. Preferred ligands are antibodies, as that term is used here, including binding fragments of antibodies. However, other natural ligands for these molecules also can be used.

B. Effector Moiety

The effector moiety may be another specific binding moiety such as an antibody, a growth factor, or a ligand. The chimeric molecule will then act as a highly specific bifunctional linker. This linker may act to bind and enhance the interaction between cells or cellular components to which the fusion protein binds.

In still yet another embodiment the effector molecule may be a pharmacological agent (e.g. a drug) or a vehicle containing a pharmacological agent. Thus, the moiety that specifically binds to TARP may be conjugated to a drug such as vinblastine, doxorubicin, genistein (a tyrosine kinase inhibitor), an antisense molecule, and other pharmacological agents known to those of skill in the art, thereby specifically targeting the pharmacological agent to tumor cells.

Alternatively, the targeting molecule may be bound to a vehicle containing the therapeutic composition. Such vehicles include, but are not limited to liposomes, micelles, various synthetic beads, and the like.

One of skill in the art will appreciate that the chimeric molecules of the present invention may include multiple targeting moieties bound to a single effector or conversely, multiple effector molecules bound to a single targeting moiety. In still other embodiments, the chimeric molecules may include both multiple targeting moieties and multiple effector molecules. Detectable labels suitable for use as the effector molecule component of the chimeric molecules of this invention include any composition detectable by spectroscopic, photochemical, biochemical, immunochemical, electrical, optical or chemical means all as described above.

One of skill will appreciate that the targeting molecule and effector molecules may be joined together in any order. Thus, where the targeting molecule is a polypeptide, the effector molecule may be joined to either the amino or carboxy termini of the targeting molecule. The targeting molecule may also be joined to an internal region of the effector molecule, or conversely, the effector molecule may be joined to an internal location of the targeting molecule, as long as the attachment does not interfere with the respective activities of the molecules.

The targeting molecule and the effector molecule may be attached by any of a number of means well known to those of skill in the art. Typically the effector molecule is conjugated, either directly or through a linker (spacer), to the targeting molecule. However, where both the effector molecule and the targeting molecule are polypeptides it is preferable to recombinantly express the chimeric molecule as a single-chain fusion protein.

In one embodiment, the targeting molecule is chemically conjugated to the effector molecule (e.g. a cytotoxin, a label, a ligand, or a drug or liposome). Means of chemically conjugating molecules are well known to those of skill. The procedure for attaching an agent to an antibody or other polypeptide targeting molecule will vary according to the chemical structure of the agent. Polypeptides typically contain variety of functional groups; e.g., carboxylic acid (COOH) or free amine (—$NH_2$) groups, which are available for reaction with a suitable functional group on an effector molecule to bind the effector thereto. Alternatively, the targeting molecule and/or effector molecule may be derivatized to expose or attach additional reactive functional groups. The derivitization may involve attachment of any of a number of linker molecules such as those available from Pierce Chemical Company, Rockford Ill.

A bifunctional linker having one functional group reactive with a group on a particular agent, and another group reactive with an antibody, may be used to form the desired immunoconjugate. Alternatively, derivitization may involve chemical treatment of the targeting molecule, e.g., glycol cleavage of the sugar moiety of a the glycoprotein antibody with periodate to generate free aldehyde groups. The free aldehyde groups on the antibody may be reacted with free amine or hydrazine groups on an agent to bind the agent thereto. (See U.S. Pat. No. 4,671,958). Procedures for generation of free sulfhydryl groups on polypeptide, such as antibodies or antibody fragments, are also known (See U.S. Pat. No. 4,659,839).

Many procedures and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. Cancer Res. 47:4071–4075 (1987). In particular, production of various immunotoxins is well-known within the art and can be found, for example in "Monoclonal Antibody-Toxin Conjugates: Aiming the Magic Bullet," Thorpe et al., MONOCLONAL ANTIBODIES IN CLINICAL MEDICINE, Academic Press, pp. 168–190 (1982), Waldmann, Science, 252:1657 (1991), U.S. Pat. Nos. 4,545,985 and 4,894,443.

Where the targeting molecule and/or the effector molecule is relatively short (i.e., less than about 50 amino acids) they may be synthesized using standard chemical peptide synthesis techniques. Where both molecules are relatively short the chimeric molecule may be synthesized as a single contiguous polypeptide. Alternatively the targeting molecule and the effector molecule may be synthesized separately and then fused by condensation of the amino terminus of one molecule with the carboxyl terminus of the other molecule thereby forming a peptide bond. Alternatively, the targeting and effector molecules may each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, Solid-Phase Peptide Synthesis; pp. 3–284 in The Peptides: Analysis, Synthesis, Biology. Vol. 2: Special Methods in Peptide Synthesis, Part A., Merrifield, et al. J. Am. Chem. Soc., 85: 2149–2156 (1963), and Stewart et al., Solid Phase Peptide Synthesis, 2nd ed. Pierce Chem. Co., Rockford, 111. (1984).

In a preferred embodiment, the chimeric fusion proteins are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins of this invention may be prepared by any suitable method, including, for example, cloning and restriction of appropriate sequences or direct chemical synthesis by methods such as the phosphotriester method of Narang et al. Meth. Enzymol. 68: 90–99 (1979); the phosphodiester method of Brown et al., Meth. Enzymol. 68: 109–151 (1979); the diethylphosphoramidite method of Beaucage et al., Tetra. Lett., 22: 1859–1862 (1981); and the solid support method of U.S. Pat. No. 4,458,066.

While the two molecules are preferably essentially directly joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins may be expressed in a variety of host cells, including E. coli, other bacterial hosts, yeast, and various higher eukaryotic cells such as the COS, CHO and HeLa cells lines and myeloma cell lines. The recombinant protein gene will be operably linked to appropriate expression control sequences for each host. For E. coli this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences. The plasmids and vectors of the invention can be transferred into the chosen host cell by well-known methods such as calcium chloride transformation for E. coli and calcium phosphate treatment or electroporation for mammalian cells.

Once expressed, the recombinant fusion proteins can be purified according to standard procedures of the art, including ammonium sulfate precipitation, affinity columns, column chromatography, gel electrophoresis and the like (see, generally, R. Scopes, PROTEIN PURIFICATION, Springer-Verlag, N.Y. (1982), Deutscher, METHODS IN ENZYMOLOGY Vol. 182: Guide to Protein Purification., Academic Press, Inc. N.Y. (1990)). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

VIII. Methods of Detecting Cells that Express TARP

In another aspect, this invention provides methods of detecting cells that express TARP. The methods involve detecting either a TARP transcript or polypeptide. Because prostate cancer cells of epithelial origin and many breast cancer cells express TARP, methods of detection are useful in the detection of prostate cancer and of TARP-expressing breast cancers. In particular, prostate cancer cells and many breast cancer cells can be distinguished from other cells by the expression of TARP.

Tissue samples can be selected from any likely site of primary or metastatic cancer including the prostate or the breast, respectively, and distal sites such as the lymph nodes and other organs. Persons of skill in the art are aware that men, as well as women, suffer from breast cancer. Breast cancer in men is relatively rare, representing only about 1% of all breast cancer cases. Because it is uncommon, however, it is frequently diagnosed at a later stage, which affects the chances for survival. Accordingly, improved diagnosis of breast cancer in men is desirable.

In one method, a biopsy is performed on the subject and the collected tissue is tested in vitro. Typically, the cells are disrupted by lysing, sonic disruption, osmotic pressure, freezing and thawing, enzymatic treatment, or other means routine in the art to render the proteins of the nucleus accesible without denaturing them. The cellular contents (or the nuclear contents, if the contents have been fractionated) are then contacted, for example, with an anti-TARP antibody. Any immune complexes which result indicate the presence of TARP in the biopsied sample. To facilitate such detection, the antibody can be radiolabeled or coupled to an effector molecule which is radiolabelled. In another method, the cells can be detected in vivo using typical imaging systems. For example, the method can involve the administration to a subject of a labeled composition capable of reaching the cell nucleus. Then, the localization of the label is determined by any of the known methods for detecting the label. Any conventional method for visualizing diagnostic imaging can be used. For example, paramagnetic isotopes can be used for MRI.

Detection of TARP

TARP can be identified by any methods known in the art. In one embodiment, the methods involve detecting the polypeptide with a ligand that specifically recognizes the polypeptide (e.g., an immunoassay). The antibodies of the invention are particularly useful for specific detection of TARP. A variety of antibody-based detection methods are known in the art. These include, for example, radioimmunoassay, sandwich immunoassays (including ELISA), immunofluorescent assays, Western blot, affinity chromatography (affinity ligand bound to a solid phase), and in situ detection with labeled antibodies. Another method for detecting TARP involves identifying the polypeptide according to its mass through, for example, gel electrophoresis, mass spectrometry or HPLC. Subject samples can be taken from any number of appropriate sources, such as saliva, peritoneal fluid, blood or a blood product (e.g., serum), urine, tissue biopsy (e.g., lymph node tissue), etc.

TARP can be detected in cells in vitro, in samples from biopsy and in vivo using imaging systems described above.

Detection of Transcript Encoding TARP

Cells that express TARP transcript can be detected by contacting the sample with a nucleic acid probe that specifically hybridizes with the transcript, and detecting hybridization. This includes, for example, methods of in situ hybridization, in which a labeled probe is contacted with the sample and hybridization is detected by detecting the attached label. However, the amounts of transcript present in the sample can be small. Therefore, other methods employ amplification, such as RT-PCR. In these methods, probes are selected that function as amplification primers which specifically amplify the TARP sequences from mRNA. Then, the amplified sequences are detected using typical methods.

The probes are selected to specifically hybridize with TARP transcripts. Generally, complementary probes are used. However, probes need not be exactly complementary if they have sufficient sequence homology and length to hybridize under stringent conditions.

IX. Pharmaceutical Compositions

In another aspect, this invention provides pharmaceutical compositions that comprise a pharmaceutically acceptable carrier and a composition of this invention.

In one embodiment, the pharmaceutical composition comprises TARP, an immunogenic fragment thereof, such as a polypeptide comprising a TARP epitope, or a TARP analog, in an amount effective to elicit a cell-mediated immune response or a humoral response in a subject, e.g., a polypeptide bearing an MHC binding motif. Such pharmaceutical compositions are useful as vaccines in the therapeutic methods of this invention and for preparing antibodies.

In another embodiment, the pharmaceutical composition comprises a nucleic acid molecule comprising a nucleotide sequence encoding a TARP polypeptide in an amount effective to elicit an immune response against cells expressing TARP in a subject. Such composition also are useful in the therapeutic methods of this invention.

In another embodiment, the pharmaceutical composition comprises a ribozyme which can specifically cleave a nucleotide sequence encoding TARP, an antisense molecule which can bind to such a nucleic acid, or an expression cassette comprising a nucleic acid encoding TARP, to modulate expression of TARP in a cell of interest.

In yet another embodiment, the pharmaceutical composition may comprise a chimeric molecule comprising a targeting molecule and a detector molecule to detect cells expressing TARP. If the detector molecule is one capable of binding specifically to a nucleic acid encoding TARP (such as a DNA binding protein which can bind specifically to DNA encoding TARP), than the composition can be used to detect cells which express that nucleic acid.

The pharmaceutical compositions of this invention can be prepared in unit dosage forms for administration to a subject. The amount and timing of administration are at the discretion of the treating physician to achieve the desired purposes.

EXAMPLES

Example 1

Detection of T-Cell Receptor γ-Chain in Prostate Cells

We identified expression of T-cell receptor γ-chain (TCRγδ mRNA in human prostate and showed that it originates from epithelial cells of the prostate and not from infiltrating T-lymphocytes. In contrast, the T-cell receptor δ-chain (TCRγδ gene is silent in human prostate. The major TCRγ transcript in prostate has a different size than the transcript expressed in thymus, spleen and blood leukocytes. It is expressed in normal prostate epithelium, adenocarcinoma of the prostate and the prostatic adenocarcinoma cell line LNCaP. The RNA originates from an unrearranged TCRγ locus and it is initiated within the intronic sequence directly upstream of the Jγ1.2 gene segment. The prostate-specific TCRγ transcript consists of the Jγ1.2 and Cγ1 gene segments, it has untranslated sequence including a polyadenylation signal and poly(A) sequence at the 3' end. The finding that prostate epithelial cells express a high level of a transcript from a gene that was thought to by exclusively expressed by T-lymphocytes is novel and highly unexpected.

1. Materials and Methods

RNA Dot Blot and Northern Blot Hybridizations

RNA dot blot (RNA master blot, Clontech, Palo Alto, Calif.), and Northern blot (MTN, Clontech, Palo Alto, Calif.), were performed on a variety of human tissues. Northern blot was also performed on mRNA from prostate adenocarcinoma cell lines, LNCaP and PC-3 (ATCC, Rockville, Md.). Isolation of poly(A) RNA was carried out using FASTTRACK™ (kit) (InVitrogen, Carlsbad, Calif.). RNA was electrophoresed on a 1% agarose gel and transferred to nylon-based membranes (GENESCREEN PLUS™, DuPont, Wilmington, Del.), according to established procedures. Ausubel, supra. A cDNA probe specific for the untranslated 3' end (3' UTR) of the TCRγ transcript was made from EST plasmid ng79d11 (Genome Systems, St. Louis, Mo.). A probe specific for the constant domain of the TCRγ transcript (TCR Cγ) was made from LNCaP cDNA and a probe for the constant domain of the TCRδ transcript (TCR Cδ) was made from a TCRδ plasmid. A human β-actin probe was used as a quantity control of the mRNA preparations. Probes were labeled with $^{32}P$ by random primer extension (Lofstrand Labs Limited, Gaithersburg, Md.) to a specific activity of 1 μCi/ng. The RNA membranes were blocked for 2 hours at 45° C. in hybridization solution containing 50% formamide (Hybrisol I, Oncor, Gaithersburg, Md.) and then probed for 15 hours at 45° C. with 20 µCi cDNA in 20 ml hybridization solution. The membranes were washed twice for 15 minutes at room temperature in 2× SSC/0.1% SDS and twice for 20 minutes at 55–65° C. in 0.1% SSC/0.1% SDS. The membranes were exposed to an imaging film (X-OMAT™, Kodak, Rochester, N.Y.) at −80° C. before development.

RNA In Situ Hybridization

The TCRγ constant domain and the TCRγ untranslated 3' end nucleotide sequence was amplified by reverse transcriptase PCR (RT-PCR) from LNCaP mRNA, cloned into pBluescript II SK (Stratagene, La Jolla, Calif.) and verified by DNA sequencing. Anti-sense and sense TCRγ $^{35}$S-riboprobes were made by T7 and T3 RNA polymerase, respectively. Paraffin blocks of 8 archived cases of prostatic transurethral resection specimens from the NCI were retrieved. Cases were selected which included both malignant and benign prostatic ducts. Average age of the cases was 69 and Gleason scores of the tumor ranged from 3+3=6/10 to 4+5=9/10. The blocks were processed on glass slides and hybridized using the riboprobes (Molecular Histology, Gaithersburg, Md.). Following hybridization the slides were counterstained with Hematoxylin and Eosin and examined using a Zeiss Axiophot Microscope equipped with a variable condenser providing bright field and dark field.

RT-PCR Analysis

Single stranded cDNAs were prepared from 150–250 ng of LNCaP and PC-3 poly(A) mRNA, respectively, using oligo-dT priming (Pharmacia-Biotech, Piscataway, N.J.). PCR primers were designed to amplify different portions of the TCRγ transcript. In order to amplify cDNA only and not trace amounts of genomic DNA, which may be present in the mRNA preparations, primer pairs were always combined to generate PCR products spanning two or more exons. One PCR was set up to amplify either of the two TCRγ constant domain genes, Cγ1 or Cγ2, with a forward primer in exon CI (TCRCγ.F) and a reverse primer in exon cm (TCRCγ.R4), FIG. 8. Variable to constant domain-spanning PCRs were set up using forward primers, specific to each of the four subgroups of TCRγ variable gene segments (TCRVγI.F, TCRVγII.F, TCRVγIII.F, TCRVγIV.F) in combination with a reverse primer in the TCRγ constant gene segment (TCRCγ.R1), FIG. 8. Wax-mediated, hot-start PCRs were conducted for 30 cycles using high-fidelity PCR components (Expand, Boehringer-Mannheim, Indianapolis, Ind.). The PCR products were analyzed on 1.2% agarose gels with 0.5 µg/ml of EtBr. Specific PCR products were gel purified (Qiagen, Valencia, Calif.), T/A cloned (InVitrogen, Carlsbad, Calif.) and sequenced on an automated capillary sequencer (Perlin Elmer Applied Systems, Foster City, Calif.), using Perkin-Elmer's dRhodamine terminator cycle sequencing kit.

Analysis of TCRγ VJ Gene Rearrangement

Genomic DNA was prepared from 5×10$^7$ LNCaP cells according to established procedures. Ausubel, supra. A set of 12 PCRs was performed, each with a forward primer from one of the four subgroup of Vγ gene segments (TCRVγI.F, TCRVγII.F, TCRVγIII.F, TCRVγIV.F) in combination with a reverse primer from one of the three Jγ1 gene segments (TCRJγ1.1.R, TCRJγ1.2.R, TCRJγ1.3.R), FIG. 8. Hot-Start PCRs were conducted for 30 cycles using 500 ng of genomic DNA and the PCRs were examined on 1.2% agarose gels with 0.5 µg/ml of EtBr. Human placenta DNA (Clontech, Palo Alto, Calif.) was used as a positive control of the primers and PCR amplification of Jγ1.1 to Jγ1.2 genomic DNA was performed as a positive control of the template.

Primer-Extension Analysis fRNA

The startpoint of the prostate TCRγ transcript was determined by primer-extension analysis of LNCaP mRNA. Five µg of mRNA was mixed with 0.08 pmol of $^{32}$P-end labeled TCRCγ.R2 primer, annealing 48–75 nucleotides from the 5' end of Cγ1. The analysis was carried out using 20 U of MMLV-reverse transcriptase (Superscript, Gibco-BRL, Gaithersburg, Md.), according to established procedure. C. P. George et al/(1996) "Primer-extension analysis of RNA" In A LABORATORY GUIDE TO RNA, ISOLATION, ANALYSIS AND SYNTHESIS. ed. P. A. Krieg. (Wiley-Liss, Inc., New York, N.Y.), pp. 133–139. The sample was electrophoresed on a 6% polyacrylamide-urea DNA sequencing gel in parallel with a $^{32}$P-end labeled molecular weight marker (MspI digested pBR322, Lofstand Labs Limited, Gaithersburg, Md.). After electrophoresis the gel was blotted to Whatman paper, dried and subjected to autoradiography.

5'-RACE PCR Analysis

Double-stranded cDNA was made from 500 ng of LNCaP poly(A) mRNA using the Marathon cDNA amplification kit (Clontech, Palo Alto, Calif.) and 25 pmole of the TCRγ gene-specific primer (TCRCγ.R3), FIG. 8. Marathon-adaptors were then ligated to the ends of the synthesized cDNA. Rapid amplification of the 5'-cDNA ends (5'-RACE) PCR was conducted using a gene-specific primer (TCRCγ.R2), FIG. 8, annealing upstream of the primer used for reverse transcription, and an adaptor-specific primer. Hot start conditions were applied (Advantage, Clontech, Palo Alto, Calif.) and the PCR products were analyzed and cloned as described for the RT-PCR analyses. DNA from the 5'-RACE PCR analytic gel was transferred to a nylon membrane and a $^{32}$P-end labeled primer (TCRCγ.R1), FIG. 8, hybridizing further upstream was applied to identify possible bands not detected by EtBr/UV.

In Vitro Transcription-Coupled Translation

The complete prostate TCRγ transcript, as obtained by RT-PCR and 5'-RACE PCR, was amplified by RT-PCR, cloned into pBluescript II SK (Stratagene, La Jolla, Calif.), sequenced and examined in an in vitro transcription-coupled translation system, using T7 RNA polymerase and wheat germ extract (TNT, Promega, Madison, Wis.). $^{35}$S-Met (ICN, Costa Mesa, Calif.) was incorporated in the reaction for visualization of translated products. The reaction was analyzed under reducing condition on a polyacrylamide gel (16.5% Tris/Tricine, BioRad, Hercules, Calif.) together with a pre-stained marker (Gibco-BRL, Gaithersburg, Md.). The gel was dried and subjected to autoradiography.

Results

A. Prostate ESTs Representing TCRγ were Identified by Database Analysis.

We identified 23 TCRγ ESTs, from 20 cDNA clones, derived from 6 tumor and 2 normal prostate cDNA libraries. The TCRγ composite sequence from assembly of prostate ESTs has 76 nucleotides of TCRγ constant domain sequence, 448 nucleotides of untranslated 3' region sequence and poly(A) sequence. By alignment of the prostate ESTs to mature TCRγ transcripts from cell lines established from peripheral blood T-lymphocytes (GenBank Acc. No. M16768, M16804 and M30894) we found that the prostate EST composite sequence is identical to the TCRγ transcript from peripheral blood T-lymphocytes. The dbEST database analysis indicates that the TCRγ gene is highly transcribed in human prostate.

B. Expression of TCRγ (3' UTR) in Human Prostate verified by RNA Dot Blot.

Figure 2:
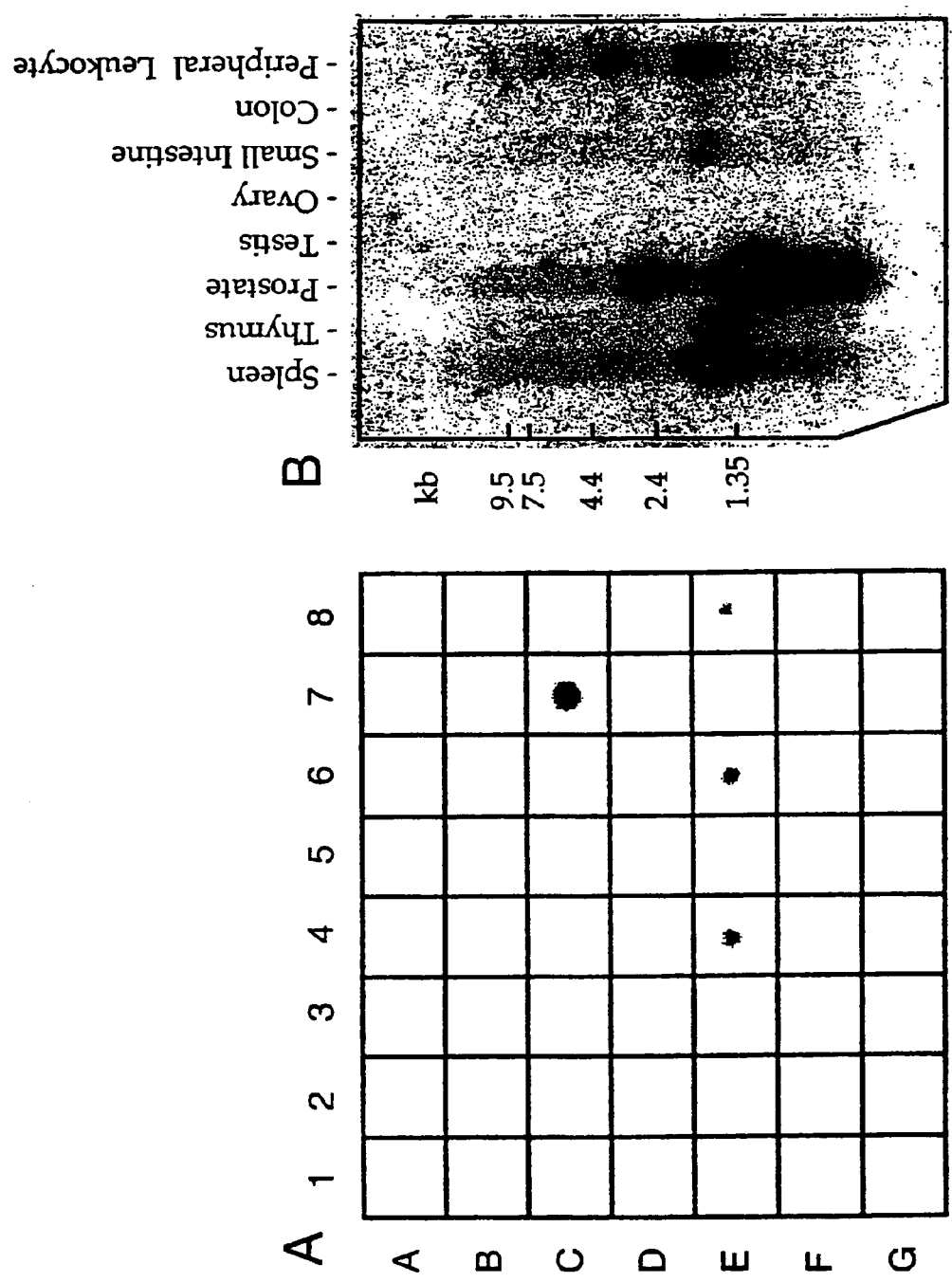
FIG. 2. Hybridization analysis of TCRγ mRNA expression.

To analyze the transcriptional activity TCRγ gene in human prostate, a cDNA probe from the untranslated 3' end (3' UTR) of the TCRγ transcript was assayed on mRNA from 50 different human tissues, FIG. 2A. We verified that normal prostate (position C7) expresses TCRγ mRNA and we further observed that prostate has by far the strongest expression of all tissues represented on the dot blot membrane. TCRγ gene expression was also found in small intestine (E3), spleen (E4), thymus (E5), peripheral leukocyte (E6), lymph node (E7), bone marrow E8), and lung (F2).

C. Northern Shows Two Size-Specific TCRγ Transcripts in Human Prostate.

Figure 3:
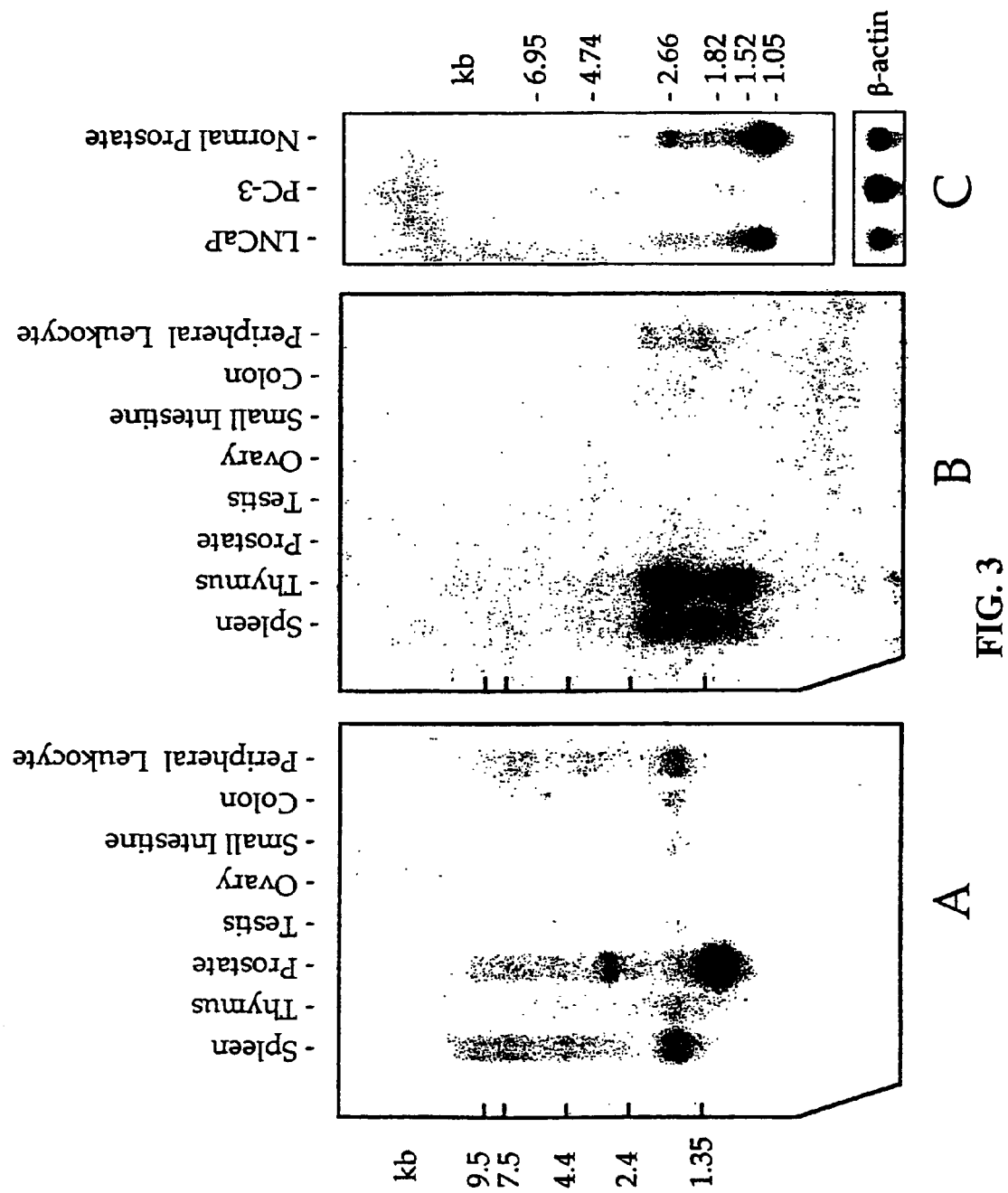
FIG. 3. Northern blot analysis of TCR γδ expression.

Northern blot hybridization using the 3' UTR probe revealed that prostate has two TCRγ transcripts of approximately 1.1 and 2.8 kb, FIG. 2B (lane 3) while the predominant transcript in spleen, thymus, small intestine and blood leukocytes is 1.5 kb. A transcript size of 1.5 kb is consistent with TCRγ mRNA from γδ T-lymphocytes (GenBank Acc. No. M16768, M16804, (Krangel et al., Science 237, 6–467 (1987)); M30894, (Littman et al. Nature 326, 85–88 (1987)). Since the database analysis indicated that a constant domain of TCRγ is part of the prostate transcript, we also used a TCRγ constant domain probe (TCR Cγ). We found the same 1.1 kb and 2.8 kb bands in the prostate, FIG. 3A (lane 3).

D. Prostate Cells Expressing TCRγ d not Express TCRδ or CD3 Transcripts.

TCR γ-chain protein is normally co-expressed with the TCR δ-chain protein. Since the TCRγ gene is transcriptionally active in human prostate, we went on to analyze the transcriptional activity of the TCRγ gene. The dbEST was analyzed on the NCBI website) using the TCRδ transcript nucleotide sequence. ESTs from prostate cDNA libraries did not match any part of the TCR δ-chain transcript. Furthermore, Northern blot analysis did not detect any prostate expression of TCRδ mRNA, FIG. 3B (lane 3). We conclude that the TCRδ gene is silent in prostate. As expected, TCRδ transcripts are expressed in spleen, thymus and blood leukocytes, FIG. 3B.

E. LNCaP Cells, but not PC-3 Cells, Express the Prostate-Specific TCRγ transcripts.

Given that TCRγ mRNA is expressed in normal prostate, we next analyzed whether it is also expressed in prostate cancer. The prostate-specific 1.1 kb transcript was found in mRNA preparations from LNCaP, but not in mRNA preparations from PC-3, FIG. 3C. The prostate-specific 2.8 kb transcript, expressed in normal prostate, is also present in LNCaP although to a much lesser degree.

A. RNA In Situ Hybridization Shows TCRγ Expression in Prostate Epithelial Cells.

Figure 4:
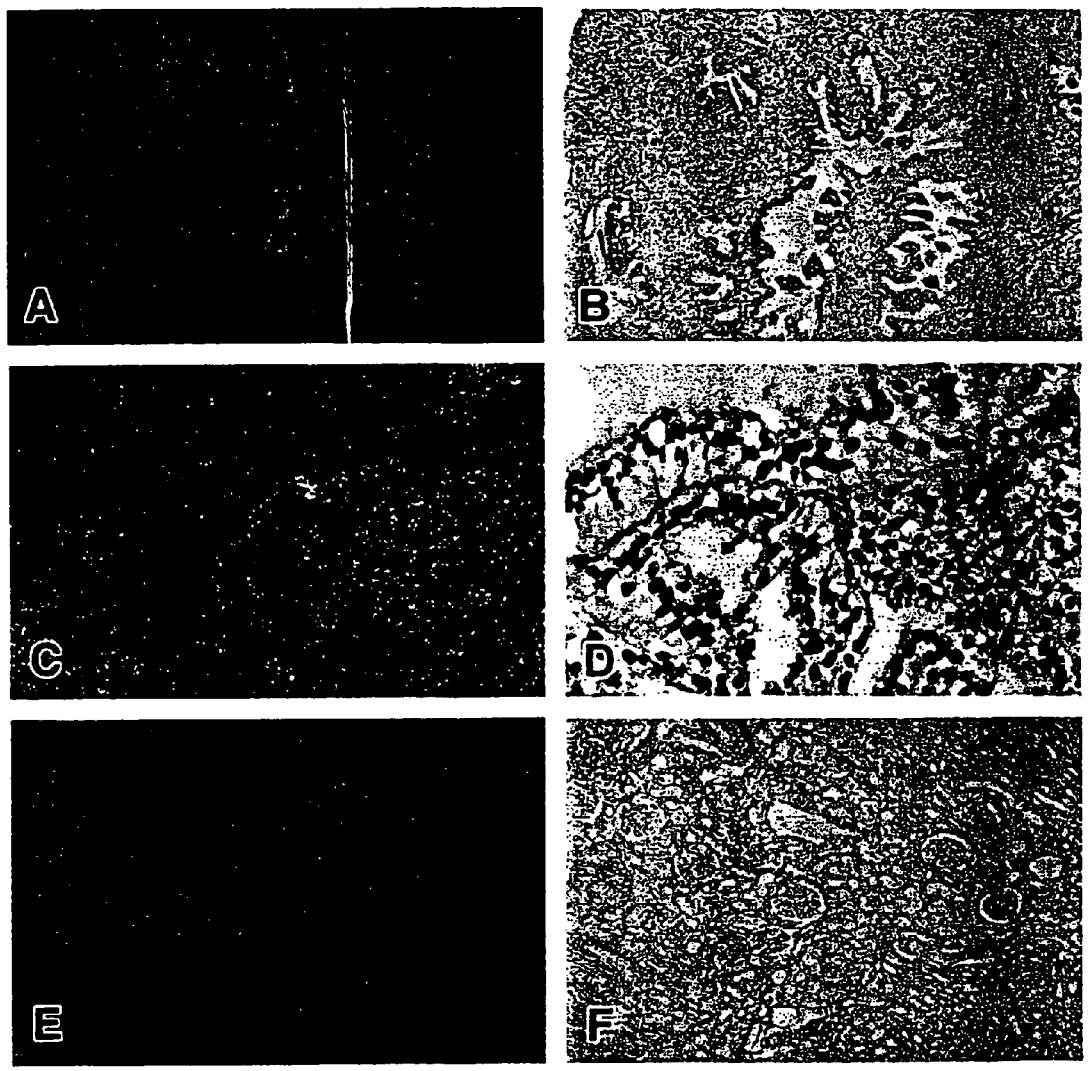
FIG. 4. RNA in situ hybridization on paraffin-embedded tissue sections using a TCRγ (Cγ1-3' UTR) anti-sense, $^{35}$S-labeled riboprobe. The left panel photos are from dark field microscopy, while the corresponding right panel photos are from in bright field microscopy. The bright grains shown in pictures taken in dark field are signals of RNA hybridization. 4A) Prostate tissues from a 67 year old man showing positive acinar epithelial cells and negative stromal cells, (5× magnification). 4B) Bright field of 4A. 4C) Higher magnification (40×) showing positive areas in the lower right corner. 4D) Bright field of 4C. 4E) Kidney tissues showing no RNA hybridization, (5× magnification). 4F) Bright field of 4E.

The prostate consists of acinar glandular tissue with variable and mixed population of simple duct lining epithelial cells, ranging to complex hyperplastic ducts in the glandular compartments. These compartments are tightly connected to smooth muscle cells, fibroblasts and other cell types in the prostate stroma To determine the cellular localization of the human prostate TCRγ expression, RNA in situ hybridization was carried out with TCR(Cγ-3' UTR) sense and anti-sense riboprobes. We found that TCRγ mRNA is highly expressed in epithelial cells within the acinar ducts of the prostate while stromal cells and other cell types in the prostate are negative, FIG. 4A, 4C. TCRγ expression was also detected in hyperplastic and neoplastic areas of the prostate. The expression in benign and neoplastic acinar epithelium is comparable. TCRγ expression could not be observed in human kidney tissue, FIG. 4E, or in human brain.

G. The Prostate TCRγ Transcript Contains Cγ1 but not any VJγ Genes.

After we had established the TCR γδ expression profile in the prostate we went on to characterize the predominant, 1.1 kb, prostate-specific TCRγ transcript. The LNCaP cell line was used for the characterization since one can not exclude the possibility of mRNA contamination from infiltrating T-cells in the mRNA preparations extracted from bulk prostate tissue. We knew from database analysis that the 3' end sequence of the prostate TCRγ transcript is identical to that from peripheral blood leukocytes and that the location of the polyadenylation signal is identical. Therefore, the difference in transcript size between prostate and leukocytes is due to sequence differences upstream of the stretch identified by the prostate ESTs. An RT-PCR set up to amplify the constant domain portion of the TCRγ transcript identified the TCRCγ1 gene. The slightly larger TCRCγ2 is not expressed in LNCaP. Variable domain (Vγ) to constant domain (Cγ)-spanning RT-PCRs did not yield any product, indicating that Vγ is not part of the prostate-specific TCRγ transcript.

H. LNCaP has not Undergone VJ Gene Rearrangement in the TCRγ Locus.

Since RT-PCRs intending to amplify the variable domain of TCRγ did not yield any product we next analyzed the TCRγ locus. During the development of γs T-cells the TCR loci undergo V(D)J gene rearrangements to bring together the gene segments that make up the variable domain of the receptor. To address whether LNCaP cells have undergone TCRγ VJ gene rearrangement PCRs were carried out on genomic DNA using combinations of TCRVγ and TCRJγ primers, to cover every possible rearrangement (see Materials and Methods). None of the primer combinations yielded any PCR product showing that LNCaP cells have not undergone VJ gene rearrangement of the TCRγ locus. The fact that TCRγ VJ rearrangement has not taken place in prostate epithelial cells, shows that the prostate expression is different from that of mature γδ T-lymphocytes.

I. Prostate Epithelial Cells Express a TCR (JC)γ Transcript.

Figure 5:
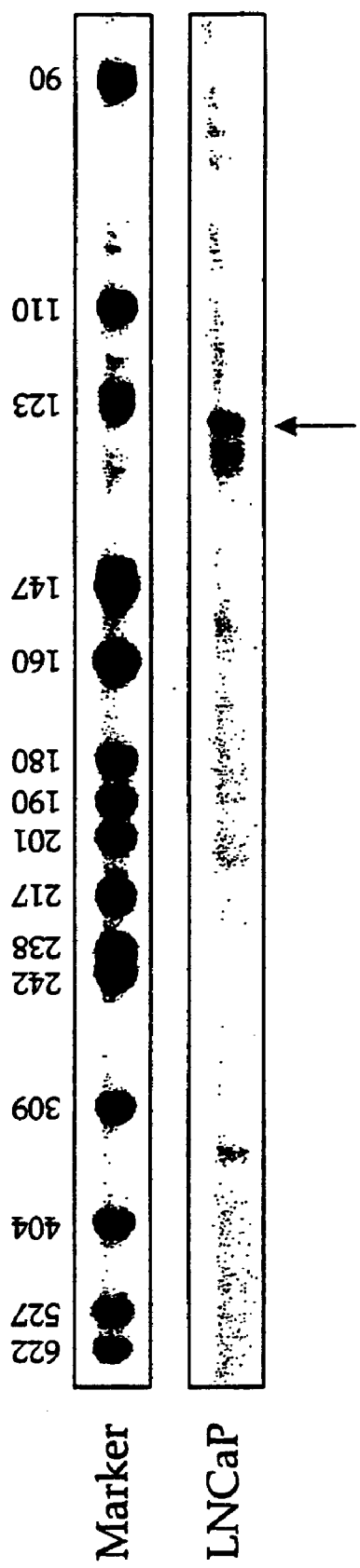
FIG. 5. Primer-extension of LNCaP mRNA. The reverse primer anneals in the constant domain of TCRγ, starting 75 nucleotides from the 5' end of Cγ1. The reverse transcription stopped at approximately 128 nucleotides, indicated by the arrow, revealing that the transcript is initiated approximately 53 nucleotides upstream of Cγ1. The lane with TCRγ reverse transcription of LNCaP was exposed for 72 hours while the marker lane was exposed for 8 hours.
Figure 6:
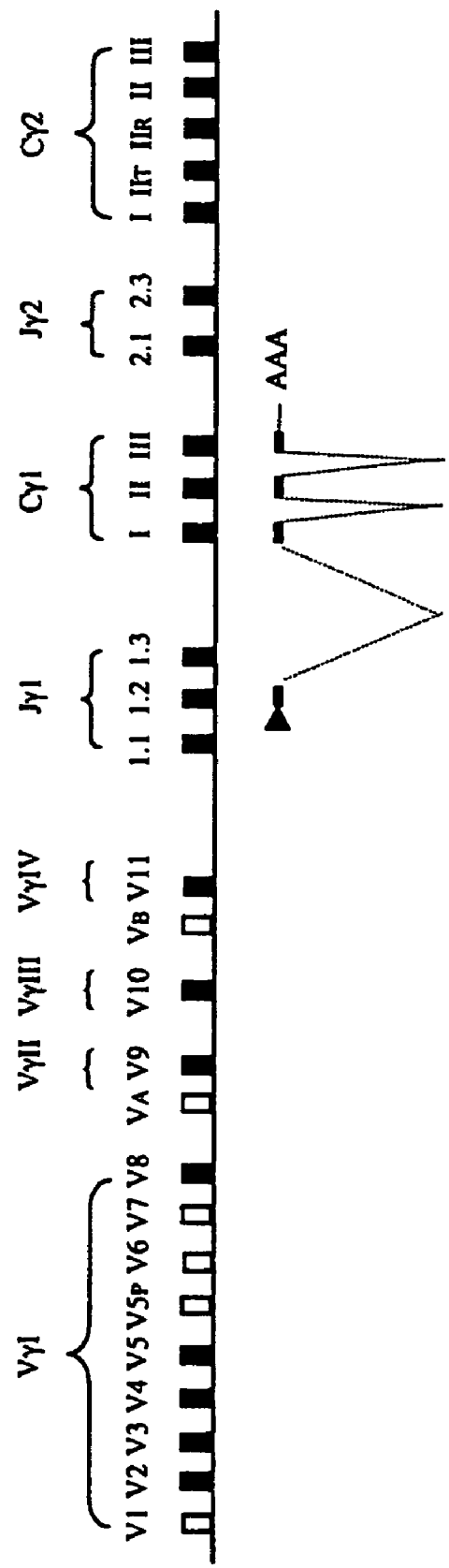
FIG. 6. The prostate TCRγ transcript. Illustration on how the prostate TCRγ is transcribed and spliced. The transcript consist of a Jγ1.2 segment, the three exons of Cγ1, followed by untranslated sequence.

Since the identified prostate TCRγ transcripts consist of Cγ but not of any Vγ gene segment, we next analyzed what sequence is upstream of Cγ1. RNA primer-extension and 5'RACE PCR were carried out to obtain the startpoint of transcription. The primer-extension experiment conducted on LNCaP mRNA, showed a predominant band of approximately 128 nucleotides with minor bands in the 130–135 nucleotide area, FIG. 5. Since the reverse transcription started 75 bases from the 5' end of Cγ1 (see Materials and Methods) the transcript has about 53 nucleotides upstream of Cγ1. The 5' RACE PCR conducted on LNCaP cDNA revealed one specific PCR product. The amplified product was found to contain a Jγ1.2 gene segment, correctly spliced to the Cγ1 gene segments. A number of clones isolated by RACE PCR were sequenced. They initiated close to the start site defined by the primer extension experiment. A somewhat variable starting point of transcription is consistent with the identification of minor bands slightly larger than the predominant one in the primer-extension experiment. An illustration of how the prostate TCRγ is transcribed and spliced is shown in FIG. 6. The nucleotide sequence of the TCRγ transcript, as obtained from LNCaP, is shown in Table 1. The composite sequence is 1020±3 nucleotides long. It contains ~53 bases from the Jγ1.2 gene segment, 519 bases of Cγ1, followed by 448 bases of untranslated sequence containing a polyadenylation signal and poly(A) sequence at the 3' end.

J. In Vitro Translation of the Prostate-Specific TCRγ Transcript.

Figure 7:
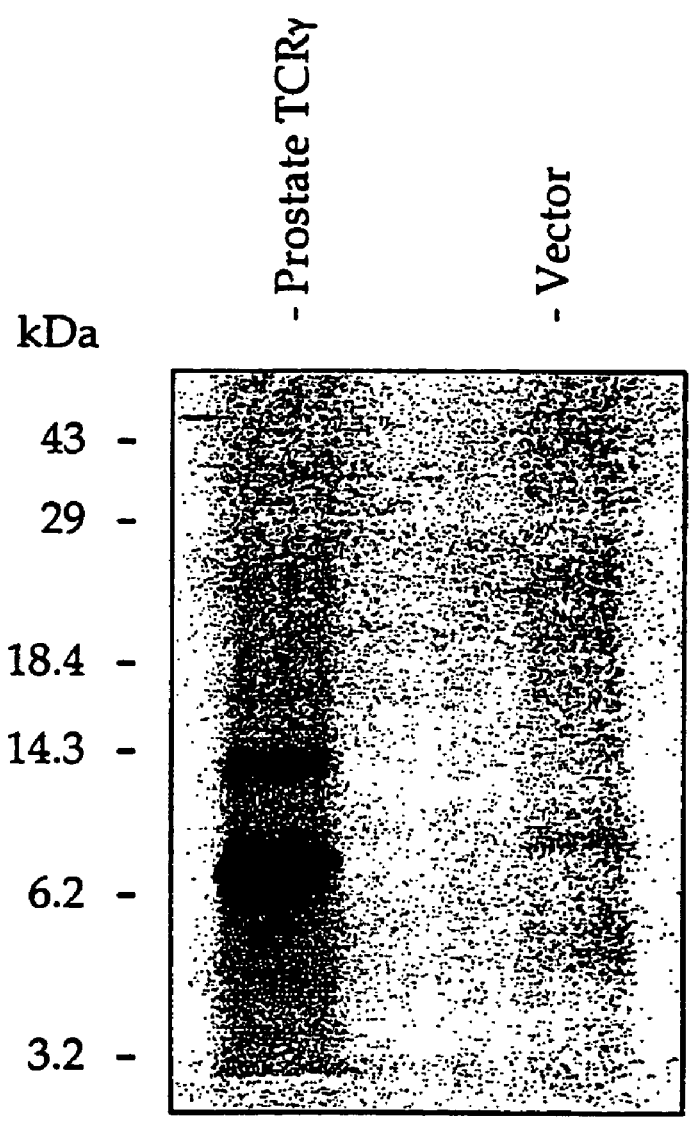
FIG. 7. In vitro transcription-coupled translation analysis of the prostate TCRγ. Two proteins with estimated sizes of 8 and 13 kDa were obtained (lane 1). Negative control reactions using the empty vector (lane 2) did not yield any protein product.
Figure 9:
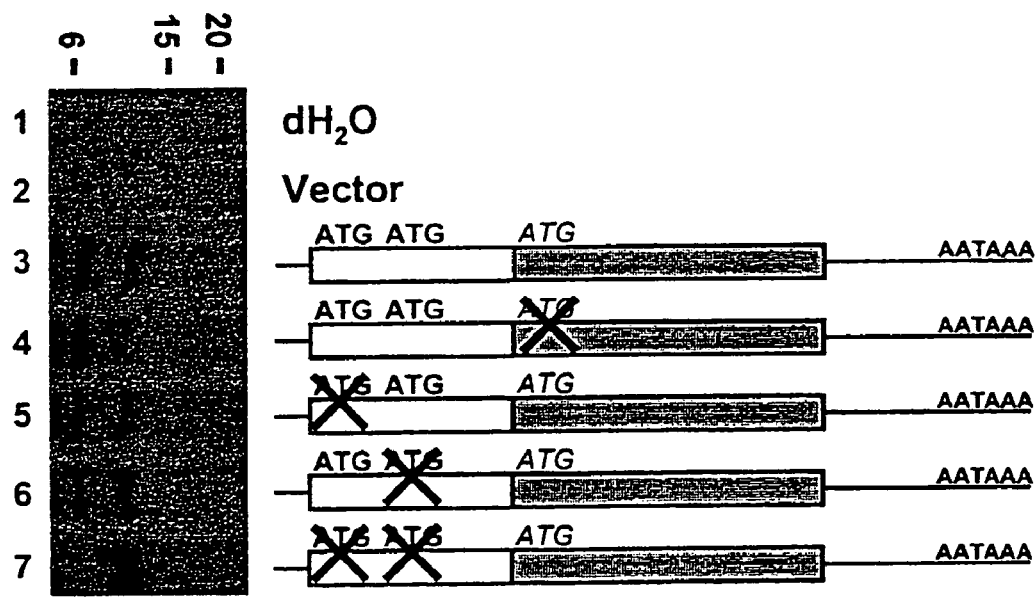
FIG. 9. In vitro translation analysis of the prostate-specific TCRγ transcript. The prostate-specific TCRγ transcript encodes two proteins in vitro. $^{35}$S-Met labeled in vitro translated proteins were run on a 16.5% Tris-Tricene gel and analyzed by autoradiography. A schematic representation of the mutant constructs used is shown on the right. An open box represents the first reading frame with potential initiation codons in bold whereas the second reading frame is represented by a shaded box with the potential initiation codon in italics. "X" indicates an ATG codon mutated to ATA. Size markers in kDa are indicated on the top.

The prostate transcript has four translational initiation codons (ATG) in the original TCRγ reading frame that are double underlined in Table 1. Calculated protein sizes for the four different start points are 12.8, 12.0, 7.2 and 3.2 kDa, respectively. To analyze the translational activity of the prostate transcript, in vitro transcription-coupled translation was carried out using full-length prostate TCRγ cDNA. Two proteins of approximately 8 and 13 kDa were obtained, FIG. 7 (lane 1). Negative control reactions did not yield any protein product.

Discussion

Specific Expression of TCRγ Transcripts in Epithelial Cells of the Prostate.

We identified expression of T-cell receptor γ-chain (TCRγ) mRNA in human prostate and have shown that it originates from epithelial cells of the prostate and not from infiltrating γγδ T-lymphocytes. We also demonstrated that the T-cell receptor δ-chain (TCRδ) gene is silent in prostate. TCRγ mRNA is expressed in epithelial cells within the acinar ducts of the prostate as well as in prostate cancer. Two TCRγ transcripts of 1.1 kb and 2.8 kb are present in human prostate. They are different in size compared to the 1.5 kb TCRγ transcript found in spleen, thymus and peripheral blood leukocytes. The TCRγδ mRNA expression profile suggests that the transcription in prostate does not follow the usual pathway of γδ T-lymphocytes. The prostate TCRγ expression was initially discovered by analysis of the publicly available EST database. Our results show that EST clustering is a powerful tool to identify novel and unexpected gene expression. The prostate ESTs representing the TCRγ transcript are all from cDNA libraries made from cells isolated by laser capture microdissection (Emmert-Buck et al., Science 274, 998–1001 (1996)). The fact that the TCRγ transcripts proved to originate from prostate epithelial cells and not from infiltrating γδ T-lymphocytes verifies that microdissection is a valuable technique to procure pure cell subpopulations from specific microscopic regions of tissues.

The Prostate TCR(JC)γTranscript.

The prostatic adenocarcinoma cell line, LNCaP, which was isolated from a lymph node metastasis (Horoszewicz et al., Cancer Res. 43, 1809–1818 (1983)) expresses readily detectable levels of the 1.1 kb prostate-specific TCRγ transcript. The expression in LNCaP cells shows that the transcript originates from epithelial cells and that it can be carried on during the development of a prostatic malignancy. The LNCaP transcript consists of 53 bases of the Jγ1.2 gene segment, the three Cγ1 exons, untranslated sequence followed by poly(A) sequence. The prostate transcript is different from the mature T-lymphocyte transcript in that it lacks a Vγ gene segment and that it is initiated within the intronic sequence directly upstream of Jγ1.2 (data not shown). The promoter driving the prostate TCRγ transcript and its mechanism of activation in prostate epithelial cells are under investigation. The 2.8 kb prostate-specific TCRγ transcript is very faint in LNCaP and the 5' RACE PCR experiment did not retrieve any product consistent with a 2.8 kb transcript. Therefore, the 2.8 kb transcript needs further study.

Comparison with TCR (JC)γ Transcripts in T-Lymphocytes.

Many studies have shown that it is possible to detect TCR gene transcription prior to, or concomitant with, the onset of V(D)J rearrangement in hematopoietic cells (Wang et al., Mol. Immunol. 33, 957–964 (1996); Shimamura, M., and Ohta, S., Eur. J. Immunol. 25, 1541–1546 (1995); Villey et al., Eur. J. Immunol. 27, 1619–1625 (1997); Sikes et al., J. Immunol. 161, 1399–1405 (1998)). The TCRγ gene has been reported to be transcriptionally active in murine bone marrow-resident T-lymphocyte precursor cells with unrearranged γ loci, resulting in sterile TCR Cγ transcripts (Wang et al., Mol. Immunol. 33, 957–964 (1996)). In addition, expression of unrearranged TCR Vγ transcripts have also been reported during ontogeny (Goldman et al. J. Exp. Med. 177, 729–739 (1993)). Sterile transcription of TCR and immunoglobulin gene segments has so far been limited to cells from the lymphoid lineages (Lauzurica, P., and Krangel, M.S., J. Exp. Med. 179, 1913–1921 (1994)). Furthermore, activation of germ-line transcription at nearly all TCR and immunoglobulin loci temporally correlates with activation of locus recombination (Sikes et al., J. Immunol. 161, 1399–1405 (1998); Goldman et al. J. Exp. Med. 177, 729–739 (1993); Lauzurica, P., and Krangel, M. S., J. Exp. Med. 179, 1913–1921 (1994); Sleckman et al., Annu. Rev. Immunol. 14, 459–481 (1996)). We have shown, by independent experiments using genomic DNA and cDNA, that recombination has not taken place of the TCRγ locus of prostate epithelial cells. Therefore, the expression of the TCR (JC)γ transcript in prostate epithelium does not correlate with recombination and it may serve a different function than the sterile transcripts observed in T-lymphocyte precursor cells.

Initial Hypothesis of the Possibility of a Novel Prostate-Specific Protein in the TCRγ Locus.

The prostate TCRγ transcript is highly expressed and we hypothesize that there is an underlying biologically important reason. The fact that VJ gene rearrangement has not taken place in the TCRγ locus of prostate epithelial cells excludes the possibility that a mature TCR γ-chain protein is made. We also exclude the possibility that a TCRγ constant domain protein is made without the TCRγ variable domain, because no translational initiation codon (ATG) is found upstream of Cγ. In TCR γ-chain proteins a Jγ segment encodes 16–20 amino acids of the variable domain, while the major part of the variable domain is encoded by one of the Vγ segments. Unless the amino acids encoded by a Jγ segment are combined with amino acids encoded by a Vγ gene segment, they cannot function as a TCR in MHC recognition. This raised the possibility of a novel prostate-specific protein, encoded from within Cγ. Our initial hypothesis was that one of the ATG codons in the original TCRγ reading frame initiates translation, although a different reading frame or a less frequently used initiation codon may be used.

The in vitro transcription-coupled translation experiment, using prostate TCRγ cDNA revealed that the transcript was fully functional. Two proteins were obtained. The 13 kDa protein most likely originates from the first double underlined ATG in FIG. 1, which yield a calculated protein size of 12.8 kDa (PS-TCRγ-1). The 8 kDa protein most likely originates from the second double underlined ATG, calculated size of 7.2 kDa (PS-TCRγ-2). These proteins were further explored in the studies reported in the next Example. In conclusion, the fact that prostate epithelial cells, or that any non-lymphoid-derived cell type, express high level of a transcript from a gene that was thought to be exclusively expressed by cells from the lymphoid lineage, was a highly unexpected discovery.

EXAMPLE 2

Discovery of the TCRγ Alternate Reading Frame Protein

The previous Example demonstrated the unexpected discovery of TCRγ transcript in prostate and prostate cancer cells, the in vitro translation of the transcript, and the initial hypothesis that the transcript resulted in the presence of a truncated form of TCRγ chain in these cells. This Example sets forth the further unexpected discovery that the transcript in fact results in a previously unknown protein, now designated "TARP," expressed from an alternate reading frame. Even more unexpectedly, the studies reported below show that TARP is a nuclear protein, and is present in many breast cancer cells.

Materials and Methods

Primers. (SEQ ID NOs.: 19–31) TCRγ-upATGmut#1 (5'-TTACAGATAAACAACTTGATACAGATGTTTCCCCC-AAGCCC-3'); TCRγ-upATGm#2 (5'-GGGCTTGGGG-GAAACATCTGTATCAAGTTGTTTATCTGTAA-3'); TCRγ-upATGm#3 (5'-GATAAACAACTTGATGCA-GATATTTCCCCCAAGCCC-3'); TCRγ-upATGm#4 (5'-GGGCTTGGGGGAAATATCTGCATCAAGT-TGTTTATC-3'); TCRγ-upATGm#5 (5'-GATAAACAA-CTTGATACAGATATTTCCCCCAAGCCC-3'); TCRγ-up-ATGm#6 (5'-GGGCTTGGGGGAAATATCTGTAT-CAAGTTGTTTATC-3'); TCRγ-downATGmut#1 (5'-CCC-AGGAGGGGGAACACCATAAAGACTAACGACACA-TAC-3'); TCRγ-downATGmut#2 (5'-GT- ATGTGTCGT-TAGTCTTTATGGTGTTCCCCCTCCTGGG-3'); TCR5.1 (5'-GATAAACAACTTGATGCAGATGTTCC-3'); TCR3.1 (5'-TTATGATTTCTCTCCATTGCAGCAG-3'); TCRJγ1.2R (5'-AAGCTTTGTTCCGGGACCAAATAC); B-Actin Forward (5'-ATCTGGCACCACACCTTCTA-CAATGAGCTGCG-3'); B-actin Reverse (5'-CTTCAT-ACTCCTGCTTGCTGATCCACATCTGC-3'). Primers were synthesized by Sigman-Genosys (The Woodsland, Tex.) and Lofstrand Labs Limited (Gaithersburg, Md.).

Constructs. The TARP transcript cloned into pBluescript II SK(+) (Stratagene, La Jolla, Calif.) was described previously (Essand, M et al., *Proc. Natl. Acad. Sci. USA* 96:9287–9292 (1999)). This plasmid is referred to as pBSSK-TCRγ in this TARP may only be functioning as a nuclear localization signal, but the fact that TARP is a nuclear protein strengthens the hypothesis that TARP may bind DNA. Functional studies are needed before any definitive conclusions can be made.

To determine if TARP shares homology with any known proteins, we performed a protein BLAST search against GenBank. This search indicated that the amino acid sequence of TARP shares some homology to *Dictyostelium dicoideum* Tup1 (GenBank accession no. AAC29438) and *Saccharomyces cerevisiae* Tup1 (Williams, F. E. et al., *Mol. Cell. Biol.* 10:6500–6511 (1990)) (FIG. 7C). Yeast Tup1 is normally found in a complex with Cyc8(Ssn6) and is required for transcriptional repression of genes that are regulated by glucose, oxygen and DNA damage (Tzamarias, D. et al., *Genes Dev.* 9:821–831 (1995)). Neither Cyc8 (Ssn6) for Tup1 binds DNA, but each acts as a part of a corepressor complex through interactions with specific DNA-binding proteins such as α2, Mig1, Rox1 and a1 (Tzamarias, D. et al., *Genes Dev.* 9:821–831 (1995)). The C'-terminal half of Tup1 contains six repeats of a 43-amino acid sequence rich in aspartate and tryptophan, known as WD-40 or β-transducin repeats (Williams, F. E. et al., *Mol. Cell. Biol.* 10:6500–6511 (1990); Fong, H. K. et al., *Proc. Natl. Acad. Sci. USA* 83:2162–2166 (1986)). WD-40 repeats have been identified in many proteins and play a role in protein—protein interactions. Importantly, Tup1 has been shown to interact with α2 through two of its WD-40 repeats (Komachi, K. et al., *Genes Dev.* 8:2857–2867 (1994)). It is interesting to note that TARP shares homology with the fifth WD-40 repeat of Tup1 (FIG. 7C). Because TARP is a nuclear protein, its homology with Tup 1 suggests that TARP may be a member of a functional nuclear protein complex involved in transcriptional regulation. Therefore, it is necessary to identify TARP-interacting proteins in order to determine its function.

The TARP antibody recognizes a doublet in prostate and breast nuclear extracts (FIG. 6A). The faster 7 kDa band comigrates with the His-TARP recombinant protein, while the weaker band runs at a larger molecular weight. One possible explanation for the 9 kDa band is post-translational modifications. To determine if TARP contains any known post-translational modification sites, we analyze the TARP amino acid sequence using the PROSITE program of the *Swiss Institute of Bioinformatics* ExPASy proteomics server (Appel, R. D. et al., *Trends Biochem. Sci.* 19:248–260 (1994); Hofmann, K et al., *Nucleic Acids Res.* 27:215–219 (1999)). As shown in FIG. 7A, many potential phosphorylation sites were found including cAMP- and cGMP-dependent protein kinase phosphorylation sites (RRAT (SEQ ID NO:32) and RRGT (SEQ ID NO:33)) and Northern Blot Hybridization. Northern blot hybridization using 2 µg of poly(A) RNA was performed as described previously (Essand, M. et al., *Proc. Natl. Acad. Sci. USA* 96:9287–9292 (1999)).

In Vitro Transcription-Coupled Translation. In vitro transcription-coupled translation reactions were described previously (Essand, M. et al., *Proc. Natl. Acad. Sci. USA* 96:9287–9292 (1999)). pBSSK-TCRγ, pBSSK-TCRγ mutATGdown, pBSSK-TCRγ mutATGup1, pBSSK-TCRγ mutATGup2 and pBSSK-TCRγ mutATGup-both were used as templates.

Cell Culture. LNCaP, PC3, MCF7, BT474 and SK-BR-3 cells were maintained in RPMI-1640 medium (Quality Biological, Inc., Gaithersburg, Md.) at 37° C. with 5% $CO_2$. The medium contained 10% fetal bovine serum (FBS, Quality Biological, Inc.), 2 mM L-glutamine, 1 mM sodium pyruvate and penicillin/streptomycin. Hs57Bst cells were maintained in RPMI-1640 medium at 37° C. with 5% $CO_2$. The medium contained 10% FBS, 30 ng/ml epidermal growth factor (EGF, Harlan, Cincinnati, Ohio), 2 mM L-glutamine, 1 mM sodium pyruvate and penicillin/streptomycin.

Antibody Production. Polyclonal APE-TARP antibodies were made as follows. pVC4D-TARP, which contains the entire TARP open reading frame fused to the C'-terminus of a catalytically inactive form of the *Pseudomonas* exotoxin (APE) (Bruggemann, E. P. et al., *BioTechniques* 10:202–209 (1991)), was expressed in Epicurian Coli® BL21-Codon-Plus™ (DE3)—RIL cells (Stratagene). Preparation of inclusion bodies and rabbit immunization were described previously (Brinkmann, U. et al., *Proc. Natl. Acad. Sci. USA* 88:8616–8620 (1991)). The antiserum was purified using the ImmunoPure® IgG (Protein A) Purification Kit according to the manufacturer's instructions (Pierce, Rockford, Ill.).

TCRγ antibodies were made as described above using pET-TCRγ, an expression plasmid containing the extracellular domain of TCRγ fused to a C'-terminal six-histidine tag. Prior to immunization, the histidine-tagged TCRγ protein was purified using a Ni-NTA agarose column according to the manufacturer's instructions (QIAGEN, Valencia, Calif.).

Preparation of Cell Extracts. Whole cell protein extracts were prepared as follows. $5 \times 10^6$ growing cells from each respective cell line were harvested and resuspended in 1× RIPA buffer containing proteinase inhibitors (50 mM Tris-HCl [pH 7.5], 150 mM NaCl, 1 mM EDTA, 0.1% TritonX-100, 1 mM PMSF, 1 μg/ml aprotinin, 1 μg/ml leupeptin). The extracts were sonicated briefly and clarified by centrifugation. Protein concentrations were determined using the Coomassie® Plus Protein Assay reagent according to the manufacturer's instructions (Pierce). Protein extracts from prostate tissue were prepared by grinding 0.5 g of prostate cancer tissue frozen at −80° C. into a fine powder using a cold mortar and pestle. The powdered tissue was collected, resuspended in 1× RIPA and processed as described above.

Nuclear, membrane and cytoplasmic extracts from prostate and breast cell lines were prepared based on protocols previously published (Dignam, J. D. et al., *Nucleic Acids Res.* 11: 1475–1489 (1983); Sladek, F. M. et al., *Genes Dev.* 4:2353–2365 (1990)).

Western Blot Analysis. 20 or 40 μg of protein extract, 1 μg of recombinant His-TARP or 100 ng of recombinant His-TCRγ were run on a 16.5% Tris-Tricene gel (BIO-RAD, Hercules, Calif.) and transferred to a 0.2 μm Immun-Blot™ PVDF membrane (BIO-RAD) in transfer buffer (25 mM Tris, 192 mM glycine, 20% (v/v) methanol, pH 8.3) at 4 CC for 4 hours at 30 V. Filters were probed with either 10 μg/ml ΔPE-TARP antiserum or 1 μg/ml TCRγ antiserum and their respective signals were detected using a chemiluminescence western blotting kit according to the manufacturer's instructions (Roche).

TARP is a nuclear protein expressed in prostate cancer cells. To determine whether TARP or TCRγ exists in prostate cancer cells, we generated antibodies against both proteins and performed western blots on different prostate cancer cell extracts. As shown in FIG. 10A (top panel), TARP was detected in the prostate cancer LNCaP cell line and a prostate cancer tumor extract. The 7 kDa band comigrates with the recombinant His-TARP suggesting that the product detected in the LNCaP and cancer extracts is TARP. Previously, we demonstrated that the prostate-specific TCRγtranscript is not expressed in the prostate cancer PC3 cell line (Essand, M. et al., *Proc. Natl. Acad. Sci. USA* 96:9287–9292 (1999)). Therefore, we used PC3 cell extracts as a negative control and demonstrated that the 7 kDa band was absent in these extracts (FIG. 10A, top panel). Importantly, no 7 kDa bands were detected when the pre-bleed antiserum or an antiserum against the *Pseudomonas* exotoxin (PE, see Materials and Methods) was used (data not shown). TCRγ was not detected in any of these extracts even though the recombinant protein showed a very strong signal with the antibody employed (FIG. 10A, bottom panel). These data indicate that the prostate-specific TCRγtranscript encodes TARP.

To determine the cellular localization of TARP, we prepared nuclear, cytoplasmic and membrane fractions from LNCaP cells. As shown in FIG. 10B, TARP was detected in the nucleus and not in the cytoplasm or membrane fraction. Similar results were obtained using nuclei purified by fractionating the cell extracts through a sucrose cushion (Sladek, F. M. et al., *Genes Dev.* 4:2353–2365 (1990)) (data not shown).

Figure 11:
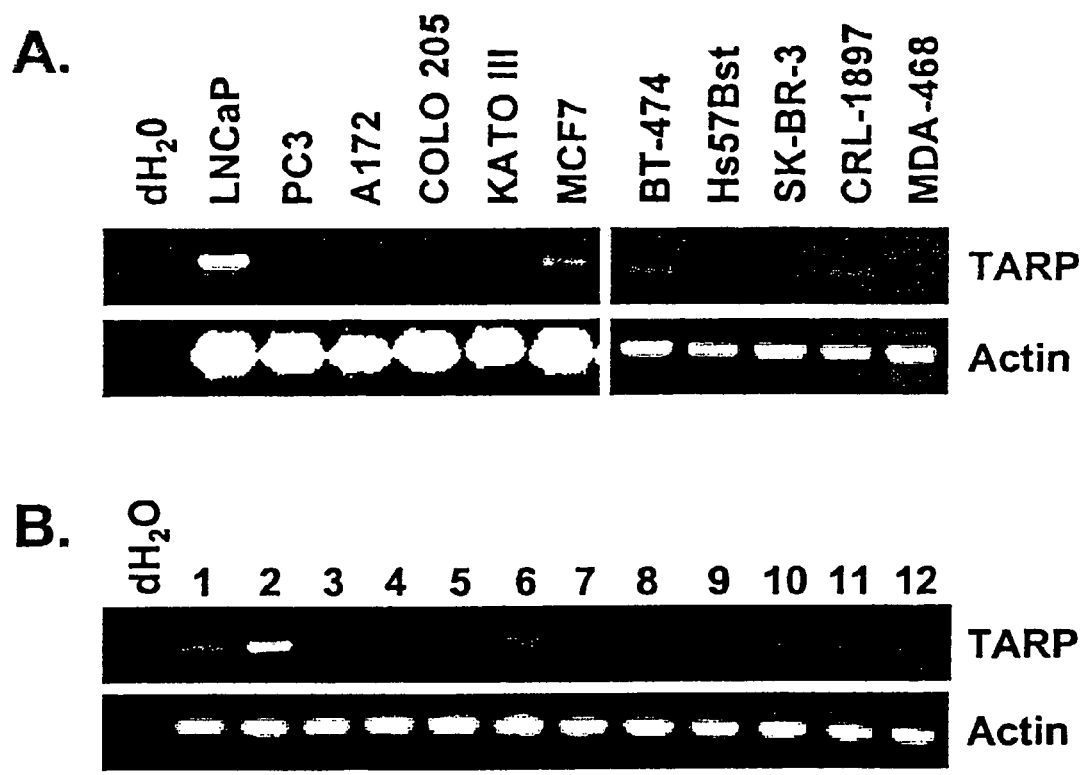
FIG. 11. TARP mRNA is expressed in breast cancer cells.

The TARP transcript is expressed in breast cells. Previously, we reported that the TCRγEST cluster also contains some ESTs from brain libraries (Vasmatzis, G. et al., *Proc. Natl. Acad. Sci. USA* 95:300–304 (1998)). After this initial report, additional ESTs have been deposited into the database and the cluster now contains ESTs from breast, colon, kidney and gastric libraries as well. To determine whether the existence of these ESTs indicates the expression of the TARP transcript in these cells or whether it may due to the presence of infiltrating γδ T-lymphocytes when these libraries were made, we performed RT-PCR on various cell lines to test for the presence of the TARP transcript. As shown in FIG. 11A, expression of the TARP transcript was detected in the breast cell lines MCF7, BT-474, SK-BR-3 and CRL-1897. No signals were detected in the neuroblastoma cell line A172, glioblastoma cell line IMR32, colon cell line COLO 205, gastric cell line KATO III or kidney cell lines COS7 and 293 (FIG. 11A and data not shown). To determine whether the TARP transcript is expressed in human breast tissues in addition to cell lines, we tested 12 different normal breast and 12 different breast cancer cDNAs using a RAPID-SCAN™ panel (OriGene Technologies, Rockville, Md.). TARP mRNA was shown to be abundant in some of the breast cancer samples (FIG. 11B, top panel) while barely detectable in the normal breast samples after 35 rounds of PCR (data not shown). Significantly, no signals were detected in reactions lacking cDNA. Actin was used to show that similar amounts of cDNA were present in each lane (bottom panel). The weak signals in the normal breast samples correlate well with the lack of TARP signal shown in FIGS. 11A and 12 for the Hs57Bst cell line, a breast cell line derived from normal breast tissue. These results suggest that expression of the TARP transcript in the breast is increased after oncogenic transformation. However, more studies are needed before any definitive conclusions can be made.

To determine whether the TARP transcript observed in the breast cell lines is the same as the transcript found in the prostate cell line, we performed RT-PCR using primers against different regions of the TARP transcript. As shown in FIG. 12A, the TARP transcript in prostate contains a portion of the Jγ1.2 gene segment, three Cγ1 exons and some untranslated sequence followed by a poly(A) tail (7). Primer set 1 and 3 amplifies the entire TARP transcript (FIG. 12B, top panel) while primer set 2 and 3 amplifies the Cγ1 region only (FIG. 12B, middle panel). As shown in FIG. 12B, similar-sized bands were detected in three breast cell lines (MCR7, BT-474 and SK-BR-3) as compared to the prostate cell line (LNCaP) using either primer set. Importantly, no signals were detected in the reactions lacking cDNA (dH2O) and similar amounts of cDNA were used as demonstrated by the actin control (FIG. 12B, bottom panel). These data indicate that the TARP transcript found in the breast cell lines is the same as the transcript found in the prostate cell line. To further support this conclusion, we analyzed the TARP transcript sizes from each cell line by a northern blot. Previously, we showed that 1100 and 2800 nucleotide transcripts exist in LNCaP cells, with the 1100 nucleotide transcript being the predominant form (Essand, M. et al., *Proc. Natl. Acad. Sci. USA* 96:9287–9292 (1999)). As shown in FIG. 12C, similar-sized TARP transcripts were found in three breast cell lines (MCF7, BT-474 and SK-BR-3) as compared to the prostate cell line (LNCaP), although at a weaker intensity. Therefore, we conclude that TARP mRNA is expressed in prostate and breast cancer cells.

To determine whether TARP protein exists in the breast cancer cell lines, we performed a western blot with breast cancer nuclear extracts using an antibody against TARP. As shown in FIG. 13 (top panel), TARP reactive bands were detected in MCF7, BT-474 and SK-BR-3 cells. TARP was not detected in the membrane or cytoplasmic fractions in these breast cancer lines (data not shown). Importantly, TARP is the protein product encoded by the TARP transcript in the breast cell lines because TCRγ was not detected in any of these nuclear extracts even though the recombinant protein showed a very strong signal with the antibody employed (FIG. 13, bottom panel). These data indicate that TARP also exists in breast cancer cells.

We report the identification of a 7 kDa nuclear protein encoded by a specific transcript derived from the TCRγ locus expressed in prostate and breast cancer cells. Because the protein is encoded from a reading frame different from TCRγ, we name it TARP for TCRγ Alternate Reading frame Protein. Besides being translated from an alternate reading frame of a transcript originating within an intron of the TCRγ locus, TARP has two other unusual features. First, it is surprising to find such a small peptide in the cell because most are usually secreted. Second, TARP lacks a good Kozak sequence (Kozak, M. Cell 44:283–92 (1986)). Because the TCRγ reading frame contains a good Kozak sequence, we initially hypothesized that a truncated TCRγ protein was encoded. However, as shown in FIG. 10, our initial hypothesis was incorrect. It is of interest that the in vitro translation results indicate a preference for the TARP protein and that either ATG in the TARP reading frame can be used to initiate protein synthesis. Protein sequencing will be needed to determine which ATG is used to initiate TARP protein synthesis.

A very interesting feature of the TARP protein sequence is that it contains five leucines in heptad repeats, suggesting that TARP may contain a leucine zipper dimerization motif (FIG. 14A). For this to be true, TARP must contain an amphipathic helix. One indication that TARP may contain an amphipathic helix is that serine and proline residues, residues believed to serve as a helix initiator, are found immediately before the first leucine repeat. Second, many charged amino acids are found within the heptad repeats thereby giving the helix an amphipathic nature and potentially serving as salt bridges with other helicies. Even though the presence of leucines in heptad repeats is a good indication of a leucine zipper motif, there are proteins identified containing five leucines in heptad repeats that are not considered leucine zipper proteins. For example, the crystal structures for karyopherin (Chook, Y. M. et al., Nature 399:230–237 (1999)), B. sterarothermophilus pyrimidine nucleoside phosphorylase (Pugmire, M. J. et al., Structure 6:1467–1479 (1998)) and T. thermophilus phenylalanyl-tRNA synthetase (Mosyak, L. et al., Nat. Struct. Biol. 2:537–547 (1995)) have shown that these proteins do not contain α-helical structures in the region where the sequence contains five leucines in heptad repeats. Interaction and structure studies are needed to determine the significance of the leucine repeats found in TARP.

Another unusual feature of the TARP amino acid sequence is that a region of basic amino acids follows the potential leucine zipper motif (FIG. 14A), suggesting a possible DNA-binding motif. However, the orientation of the basic region is rather unique in that it follows the leucine repeats rather than precedes them. Most leucine zipper proteins that bind DNA have the basic region before the leucine repeats (for a review, see (Chook, Y. M. et al., Nature 399:230–237 (1999))). The basic region in TARP may only be functioning as a nuclear localization signal, but the fact that TARP is a nuclear protein strengthens the hypothesis that TARP may bind DNA. Functional studies are needed before any definitive conclusions can be made.

To determine if TARP shares homology with any known proteins, we performed a protein BLAST search against GENBANK® (database). This search indicated that the amino acid sequence of TARP shares some homology to *Dictyostelium dicoideum* Tup1 (GENBANK® (database) accession no. AAC29438) and *Saccharomyces cerevisiae* Tup1 (Williams, F. E. et al., Mol. Cell. Biol. 10:6500–6511 (1990)) (FIG. 14B). Yeast Tup1 is normally found in a complex with Cyc8(Ssn6) and is required for transcriptional repression of genes that are regulated by glucose, oxygen and DNA damage (Tzamarias, D. et al., Genes Dev. 9:821–831 (1995)). Neither Cyc8(Ssn6) nor Tup1 binds DNA, but each acts as a part of a corepressor complex through interactions with specific DNA-binding proteins such as α2, Mig1, Rox1 and a1 (Tzamarias, D. et al., Genes Dev. 9:821–831 (1995)). The C'-terminal half of Tup1 contains six repeats of a 43-amino acid sequence rich in aspartate and tryptophan, known as WD-40 or β-transducin repeats (Williams, F. E. et al., Mol. Cell. Biol. 10:6500–6511 (1990); Fong, H. K. et al., Proc. Natl. Acad. Sci. USA 83:2162–2166 (1986)). WD-40 repeats have been identified in many proteins and play a role in protein—protein interactions. Importantly, Tup1 has been shown to interact with α2 through two of its WD-40 repeats (Komachi, K. et al., Genes Dev. 8:2857–2867 (1994)). It is interesting to note that TARP shares homology with the fifth WD-40 repeat of Tup1 (FIG. 14B). Because TARP is a nuclear protein, its homology with Tup1 suggests that TARP may be a member of a functional nuclear protein complex involved in transcriptional regulation. Therefore, it is necessary to identify TARP-interacting proteins in order to determine its function.

The TARP antibody recognizes a doublet in prostate and breast nuclear extracts (FIG. 13A). The faster 7 kDa band comigrates with the His-TARP recombinant protein, while the weaker band runs at a larger molecular weight. One possible explanation for the 9 kDa band is post-translational modifications. To determine if TARP contains any known post-translational modification sites, we analyze the TARP amino acid sequence using the PROSITE program of the *Swiss Institute of Bioinformatics* ExPASy proteomics server [available on the internet] (Appel, R. D. et al., Trends Biochem. Sci. 19:248–260 (1994); Hofmann, K et al., Nucleic Acids Res. 27:215–219 (1999)). As shown in FIG. 14A, many potential phosphorylation sites were found including cAMP- and cGMP-dependent protein kinase phosphorylation sites (RRAT (SEQ ID NO:32) and RRGT (SEQ ID NO:33)) and protein kinase C phosphorylation sites (SSR and SRR). Phosphorylation has been shown in many cases to cause a protein to run at a larger apparent molecular weight on an SDS-PAGE gel. If this is the case, the results from FIG. 6 may indicate that the unmodified form is prevalent in LNCaP cells and that only the phosphorylated form is present in MCF7 and SK-BR-3 cells. Additional experiments are clearly needed to determine the true nature of the 9 kDa band and whether TARP is post-translationally modified when expressed in prostate and breast cancer cells.

We report here the expression of TARP mRNA and protein in breast cancer cells. Our initial studies of the TARP transcript did not reveal TARP expression in the breast (Essand, M. et al., Proc. Natl. Acad. Sci. USA 96:9287–9292

(1999)). One possible explanation is that TARP is expressed at low levels in the normal breast and is difficult to detect. As described in the Results section, very weak signals were detected in a PCR analysis of normal breast samples as compared to the strong signals detected in the cancer samples. Therefore, the presence of TARP in breast cancer cells may indicate that TARP expression is induced after the oncogenic transformation of breast cells. In addition, the existence of TARP in breast cancer cells may indicate that TARP is regulated by estrogen. This hypothesis is strengthened by the identification of an element within the intronic promoter of TARP that combines an androgen response element (ARE) with an estrogen response element (ERE). This hybrid element consists of two half-sites specific to the ARE at the 5' end and to the ERE at the 3' end [(Zilliacus, J. et al., *Mol. Endocrinol.* 9:389400 (1995)) and unpublished data)]. Additional experiments are needed to determine if estrogen regulates TARP. There are instances, however, where mutant AREs cause the expression of certain prostate-specific genes in breast tumors. For example, prostate specific antigen (PSA) has been shown to be expressed in breast tumors (Majumdar, S. et al., *Br. J. Cancer* 79:1594–1602 (1999)). Molecular analysis of the aberrant expression of PSA lead to the discovery of a single point mutation in one of the AREs found within the PSA promoter. It is believed that this mutation leads to the loss of androgen-regulated PSA expression in breast tumors (Majumdar, S. et al., *Br. J. Cancer* 79:1594–1602 (1999)). It is unclear at this time whether a similar mutation in the TARP promoter occurs in the three breast cell lines tested.

The prostate is dependent on androgens for maintenance of its structure and function. When prostate cells become malignant, they often lose their androgen dependence. In this study, we used two prostate cell lines that differ in their dependence on androgen for growth: LNCaP and PC3 cells. The androgen receptor is present in the androgen-dependent LNCaP cell line, but is absent in the androgen-independent PC3 cell line (Tilley, W. D. et al., *Cancer Res.* 50:5382–5386 (1990)). As shown in FIG. 10, TARP is expressed in LNCaP cells but not in PC3 cells. This result suggests that TARP expression may be regulated by androgen stimulation. The identification of an ARE-like element within the TARP promoter strengthens the idea that TARP is induced by androgens. Experiments are currently being done to determine whether androgens induce TARP mRNA expression. Expression in LNCaP cell but not in PC3 cells may indicate that TARP is important in regulating androgen-dependent responses.

The present invention provides novel materials and methods relating, inter alia, to prostate cells, prostate cancer, and breast cells and breast cancer. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document Applicants do not admit that any particular reference is "prior art" to their invention.

What is claimed is:

1. A substantially purified polypeptide comprising the amino acid sequence set forth as SEQ ID NO: 14.

2. A composition comprising the polypeptide of claim 1 and a pharmaceutically acceptable carrier.

3. A substantially purified recombinant nucleic acid molecule consisting of the polynucleotide sequence set forth as nucleotides 74 to 247 of SEQ ID NO: 13, or a degenerate variant thereof, wherein the recombinant nucleic acid or the degenerate variant thereof encodes the polypeptide of claim 1.

4. A substantially purified recombinant nucleic acid molecule comprising
   (a) a nucleic acid molecule consisting of the polynucleotide sequence set forth as nucleotides 74 to 247 of SEQ ID NO: 13, or a degenerate variant thereof, wherein the recombinant nucleic acid or the degenerate variant thereof encodes the polypeptide of claim 1; and
   (b) a promoter.

5. A vector comprising the substantially purified recombinant nucleic acid molecule of claim 4.

6. A substantially purified polypeptide consisting of eight to ten consecutive amino acids of the amino acid sequence as set forth as SEQ ID NO: 14, wherein the polypeptide has a leucine or a methionine at the second position and valine or leucine in the last position, and wherein the polypeptide specifically binds HLA-A2.

7. A composition comprising the polypeptide of claim 6 and a pharmaceutically acceptable carrier.

8. A substantially purified recombinant nucleic acid molecule encoding the polypeptide of claim 6.

9. The substantially purified recombinant nucleic acid molecule of claim 8, operably linked to a promoter.

10. A vector comprising the substantially purified recombinant nucleic acid molecule of claim 9.

11. A substantially purified fusion polypeptide comprising the polypeptide of claim 6 and a second different polypeptide moiety.

12. A method for eliciting an immune response in a subject, comprising administering to a subject a composition comprising the fusion polypeptide of claim 11, thereby eliciting the immune response in the subject.

13. The substantially purified fusion polypeptide of claim 11, wherein the second different polypeptide moiety is selected from the group consisting of a polypeptide tag for isolation, a carrier protein, and a linker.

14. A composition comprising the fusion polypeptide of claim 11 and a pharmaceutically acceptable carrier.

15. A nucleic acid encoding the fusion polypeptide of claim 11.

16. The nucleic acid of claim 15, operably linked to a promoter.

17. A substantially purified recombinant nucleic acid molecule encoding the fusion polypeptide of claim 11.

18. The substantially purified recombinant nucleic acid molecule of claim 17, operably linked to a promoter.

19. A vector comprising the substantially purified recombinant nucleic acid molecule of claim 18.

20. A method for eliciting an immune response in a subject, comprising administering to a subject a composition comprising:
    (a) a substantially purified polypeptide comprising the amino acid sequence set forth as SEQ ID NO: 14; or
    (b) a substantially purified polypeptide consisting of eight to ten consecutive amino acids of the amino acid sequence as set forth as SEQ ID NO: 14, wherein the polypeptide has a leucine or a methionine at the second position and valine or leucine in the last position, and wherein the polypeptide specifically binds HLA-A2;
in a pharmaceutically acceptable carrier, thereby eliciting the immune response in the subject.

21. The method of claim 20 wherein the subject has prostate cancer.

22. The method of claim 20, wherein the subject has breast cancer.

23. The method of claim 20, wherein the composition is administered to a female subject.

24. The method of claim 20, further comprising co-administering to the subject an immune adjuvant selected from the group consisting of a non-specific immune adjuvant, a subcellular microbial product, a subcellular microbial fraction, a hapten, an immunogenic protein, an immunomodulator, an interferon, a thymic hormone, and a colony stimulating factor.

25. The method of claim 20, comprising administering the substantially purified polypeptide comprising the amino acid sequence set forth as SEQ ID NO: 14.

26. The method of claim 20, comprising administering the substantially purified polypeptide consisting of at eight to ten consecutive amino acids of the amino acid sequence as set forth as SEQ ID NO: 14, wherein the polypeptide has a leucine or a methionine at the second position and valine or leucine in the last position, and wherein the polypeptide specifically binds HLA-A2.

27. The method of claim 20 further comprising administering to the subject CD8+ cells that are sensitized with antigen presenting cells pulsed with (a) a polypeptide consisting of an epitope of eight to ten consecutive amino acids of the protein having the amino acid sequence as set forth as SEQ ID NO: 14 or (b) a polypeptide consisting of an epitope of eight to ten consecutive amino acids of the protein having the amino acid set forth as SEQ ID NO: 14 and a second different polypeptide moiety.

28. The method of claim 27 wherein the CD8+ cells are cytotoxic T lymphocytes.

29. The method of claim 28 wherein the cytotoxic T lymphocytes are tumor infiltrating lymphocytes.

30. A substantially purified recombinant nucleic acid of claim 10, eemprising consisting of the nucleic acid sequence as set forth as SEQ ID NO: 13.

31. A method for eliciting an immune response in a subject comprising administering to a subject a composition comprising a fusion polypeptide comprising a polypeptide moiety consisting of at eight to ten consecutive amino acids of the amino acid sequence as set forth as SEQ ID NO: 14, wherein the polypeptide has a leucine or a methionine at the second position and valine or leucine in the last position, and wherein the polypeptide specifically binds HLA-A2, and further comprising a second different polypeptide moiety.

* * * * *

SEQUENCE LISTING

```
<160> NUMBER OF SEQ ID NOS: 33

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence:PCR primer

<400> SEQUENCE: 1
aacttggaag ggrgaacraa gtcagtc                                        27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:PCR primer

<400> SEQUENCE: 2
agtactaaaa cgctgtcaaa aacagcc                                        27

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 3
```

```
ttggacttgg attatcaaaa gtgg                                          24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 4
ttgggcagtt ggaacaacct gaaa                                          24

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence:PCR primer

<400> SEQUENCE: 5
gataaacaac ttgatgcaga tgtttccc                                      28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence:PCR primer

<400> SEQUENCE: 6
gggaaacatc tgcatcaagt tgtttatc                                      28

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:PCR primer

<400> SEQUENCE: 7
ctggagcttt gtttcagcaa ttgaagg                                       27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:PCR primer

<400> SEQUENCE: 8
ctcaagaaga caaaggtatg ttccagc                                       27

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 9
ttatgatttc tctccattgc agcag                                         25

<210> SEQ ID NO 10
<211> LENGTH: 25
<212> TYPE: DNA
```

```
<213> ORGANISM: Artificial Sequence
<220> FEATURE:
<223> OTHER INFORMATION: Description of Artificial Sequence:PCR primer

<400> SEQUENCE: 10
gaagttacta tgagcttagt ccctt                                          25

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 11
aagctttgtt ccgggaccaa atac                                           24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 12
tacctgtgac aacaagtgtt gttc                                           24

<210> SEQ ID NO 13
<211> LENGTH: 1027
<212> TYPE: DNA
<213> ORGANISM: Homo sapiens
<220> FEATURE:
<221> NAME/KEY: CDS
<222> LOCATION: (74)..(247)
<223> OTHER INFORMATION: Coding region for PS-TCR gamma 1 polypeptide
      (TARP)
<220> FEATURE:
<221> NAME/KEY: CDS
<222> LOCATION: (247)..(579)
<223> OTHER INFORMATION: Coding region for PS-TCR gamma 2 polypeptide (deduced amino
      acid sequence not displayed along with DNA sequence, due to
      overlapping CDS's)

<400> SEQUENCE: 13
gggcaagagt tgggcaaaaa atcaaggta tttggtcccg gaacaaagct tatcattaca      60
gataaacaac ttg atg cag atg ttt ccc cca agc cca cta ttt ttc ttc      109
             Met Gln Met Phe Pro Pro Ser Pro Leu Phe Phe Phe
               1               5                  10 ctt caa ttg ctg aaa caa agc tcc aga agg ctg gaa cat acc ttt gtc    157
Leu Gln Leu Leu Lys Gln Ser Ser Arg Arg Leu Glu His Thr Phe Val
        15                  20                  25 ttc ttg aga aat ttt tcc ctg atg tta tta aga tac att ggc aag aaa    205
Phe Leu Arg Asn Phe Ser Leu Met Leu Leu Arg Tyr Ile Gly Lys Lys
     30                  35                  40 aga aga gca aca cga ttc tgg gat ccc agg agg gga aca cca               247
Arg Arg Ala Thr Arg Phe Trp Asp Pro Arg Arg Gly Thr Pro
 45                  50                  55 tgaagactaa cgacacatac atgaaattta gctggttaac ggtgccagaa aagtcactgg     307
acaaagaaca cagatgtatc gtcagacatg agaataataa aaacggagtt gatcaagaaa     367
ttatctttcc tccaataaag acggatgtca tcacaatgga tcccaaagac aattgttcaa     427
aagatgcaaa tgatacacta ctgctgcagc tcacaaacac ctctgcatat tacatgtacc     487
tcctcctgct cctcaagagt gtggtctatt ttgccatcat cacctgctgt ctgcttagaa     547
```

```
gaacggcttt ctgctgcaat ggagagaaat cataacagac ggtggcacaa ggaggccatc      607
tttccctcat cggttattgt ccctagaagc gtcttctgag gatctagttg ggctttcttt      667
ctgggtttgg gccatttcag ttctcatgtg tgtactattc tatcattatt gtataacggt      727
tttcaaacca gtgggcacac agagaacctc actctgtaat aacaatgagg aatagccacg      787
gcgatctcca gcaccaatct ctccatgttt tccacagctc ctccagccaa cccaaatagc      847
gcctgctata gtgtagacat cctgcggctt ctagccttgt ccctctctta gtgttcttta      907
atcagataac tgcctggaag cctttcattt tacacgccct gaagcagtct tctttgctag      967
ttgaattatg tggtgtgttt ttccgtaata agcaaaataa atttaaaaaa atgaaaagtt     1027
```

<210> SEQ ID NO 14
<211> LENGTH: 58
<212> TYPE: PRT
<213> ORGANISM: Homo sapiens

<400> SEQUENCE: 14

```
Met Gln Met Phe Pro Pro Ser Pro Leu Phe Phe Leu Gln Leu Leu
  1               5                  10                  15

Lys Gln Ser Ser Arg Arg Leu Glu His Thr Phe Val Phe Leu Arg Asn
                 20                  25                  30

Phe Ser Leu Met Leu Leu Arg Tyr Ile Gly Lys Lys Arg Arg Ala Thr
             35                  40                  45

Arg Phe Trp Asp Pro Arg Arg Gly Thr Pro
         50                  55
```

<210> SEQ ID NO 15
<211> LENGTH: 111
<212> TYPE: PRT
<213> ORGANISM: Homo sapiens

<400> SEQUENCE: 15

```
Met Lys Thr Asn Asp Thr Tyr Met Lys Phe Ser Trp Leu Thr Val Pro
  1               5                  10                  15

Glu Lys Ser Leu Asp Lys Glu His Arg Cys Ile Val Arg His Glu Asn
                 20                  25                  30

Asn Lys Asn Gly Val Asp Gln Glu Ile Ile Phe Pro Pro Ile Lys Thr
             35                  40                  45

Asp Val Ile Thr Met Asp Pro Lys Asp Asn Cys Ser Lys Asp Ala Asn
         50                  55                  60

Asp Thr Leu Leu Leu Gln Leu Thr Asn Thr Ser Ala Tyr Tyr Met Tyr
 65                  70                  75                  80

Leu Leu Leu Leu Leu Lys Ser Val Val Tyr Phe Ala Ile Ile Thr Cys
                 85                  90                  95

Cys Leu Leu Arg Arg Thr Ala Phe Cys Cys Asn Gly Glu Lys Ser
                100                 105                 110
```

<210> SEQ ID NO 16
<211> LENGTH: 16
<212> TYPE: PRT
<213> ORGANISM: Homo sapiens
<220> FEATURE:
<223> OTHER INFORMATION: Partial amino acid sequence of TARP (residues 42-57)

<400> SEQUENCE: 16

```
Gly Lys Lys Arg Arg Ala Thr Arg Phe Trp Asp Pro Arg Arg Gly Thr
  1               5                  10                  15
```

```
<210> SEQ ID NO 17
<211> LENGTH: 16
<212> TYPE: PRT
<213> ORGANISM: Dictyostelium discoideum
<220> FEATURE:
<223> OTHER INFORMATION: Partial amino acid sequence of Tup1 (dTup,
      residues 521-536)

<400> SEQUENCE: 17

Gly Ser Lys Asp Arg Ser Val Gln Phe Trp Asp Pro Arg Asn Gly Thr
 1               5                  10                  15

<210> SEQ ID NO 18
<211> LENGTH: 16
<212> TYPE: PRT
<213> ORGANISM: Saccharomyces cerevisiae
<220> FEATURE:
<223> OTHER INFORMATION: Partial amino acid sequence of Tup1 (yTup1,
      residues 626-660)

<400> SEQUENCE: 18

Gly Ser Lys Asp Arg Gly Val Leu Phe Trp Asp Lys Lys Ser Gly Asn
 1               5                  10                  15

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence:PCR primer

<400> SEQUENCE: 19
ttacagataa acaacttgat acagatgttt cccccaagcc c                 41

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence:PCR primer

<400> SEQUENCE: 20
gggcttgggg gaaacatctg tatcaagttg tttatctgt                    39

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence:PCR primer

<400> SEQUENCE: 21
gataaacaac ttgatgcaga tatttccccc aagccc                       36

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence:PCR primer

<400> SEQUENCE: 22
gggcttgggg gaaatatctg catcaagttg tttatc                       36

<210> SEQ ID NO 23
<211> LENGTH: 36
```

```
<212> TYPE: DNA
<213> ORGANISM: Artificial Sequence
<220> FEATURE:
<223> OTHER INFORMATION: Description of Artificial Sequence:PCR primer

<400> SEQUENCE: 23
gataaacaac ttgatacaga tatttccccc aagccc                                  36

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence:PCR primer

<400> SEQUENCE: 24
gggcttgggg gaaatatctg tatcaagttg tttatc                                  36

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence:PCR primer

<400> SEQUENCE: 25
cccaggaggg gaacaccata aagactaacg acacatac                                38

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence:PCR primer

<400> SEQUENCE: 26
gtatgtgtcg ttagtcttta tggtgttccc ctcctggg                                38

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 27
gataaacaac ttgatgcaga tgttt                                              25

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 28
ttatgatttc tctccattgc agcag                                              25

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 29
```

```
aagctttgtt ccgggaccaa atac                                                  24

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence:PCR primer

<400> SEQUENCE: 30
atctggcacc acaccttcta caatgagctg cg                                         32

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence:PCR primer

<400> SEQUENCE: 31
cttcatactc ctgcttgctg atccacatct gc                                         32

<210> SEQ ID NO 32
<211> LENGTH: 4
<212> TYPE: PRT
<213> ORGANISM: Homo sapiens
<220> FEATURE:
<223> OTHER INFORMATION: Protein kinase phosphorylation site

<400> SEQUENCE: 32

Arg Arg Ala Thr
 1

<210> SEQ ID NO 33
<211> LENGTH: 4
<212> TYPE: PRT
<213> ORGANISM: Homo sapiens
<220> FEATURE:
<223> OTHER INFORMATION: Protein kinase phosphorylation site

<400> SEQUENCE: 33

Arg Arg Gly Thr
 1
```